(12) United States Patent
De Oliveira et al.

(10) Patent No.: US 11,849,701 B2
(45) Date of Patent: Dec. 26, 2023

(54) APPARATUS AND METHOD FOR PUPAE SEPARATION

(71) Applicant: Forrest Innovations Ltd., Rehovot (IL)

(72) Inventors: Deborah Aline De Oliveira, Piraquara (BR); Aline De Oliveira Da Rosa, Curitiba (BR); Lisiane De Castro Poncio, Curitiba (BR); Débora Rebechi, Curitiba (BR)

(73) Assignee: FORREST INNOVATIONS LTD., Rehovot (IL)

( * ) Notice: Subject to any disclaimer, the term of this patent is extended or adjusted under 35 U.S.C. 154(b) by 0 days.

(21) Appl. No.: 17/880,982

(22) Filed: Aug. 4, 2022

(65) Prior Publication Data
US 2023/0045919 A1   Feb. 16, 2023

(30) Foreign Application Priority Data
Aug. 11, 2021   (IL) .......................................... 285542

(51) Int. Cl.
*A01K 1/08*   (2006.01)
*A01K 67/033*   (2006.01)

(52) U.S. Cl.
CPC .............. *A01K 1/08* (2013.01); *A01K 67/033* (2013.01)

(58) Field of Classification Search
CPC ................................. A01K 1/08; A01K 67/033
See application file for complete search history.

(56) References Cited

U.S. PATENT DOCUMENTS

| | | | | |
|---|---|---|---|---|
| 3,223,237 A * | 12/1965 | Harrod, Jr. | ........... | A01K 67/033 209/675 |
| 11,440,057 B2 * | 9/2022 | Greeley | .................... | B07C 5/36 |
| 2015/0008163 A1 * | 1/2015 | Nimmo | ................ | B07B 1/4636 209/676 |
| 2019/0191677 A1 | 6/2019 | Massaro | | |
| 2021/0076637 A1 | 3/2021 | Van Kilsdonk et al. | | |
| 2021/0346913 A1 * | 11/2021 | Greeley | .................... | B07B 1/46 |

OTHER PUBLICATIONS

Translation of CN 109042544 A; "Automatic Mosquito Pupa Separator and Separation Method"; published date Dec. 21, 2018 (Year: 2018).*
Translation of CN 109261492 A; Huang, Zhi-gang et al.; "A Hydraulic Tipping Vibration Sieve Device and Using Method Thereof"; published date Jan. 25, 2019 (Year: 2019).*
Araújo et al., (2015) Aedes aegypti Control Strategies in Brazil: Incorporation of New Technologies to Overcome the Persistence of Dengue Epidemics. Insects 6(2): 576-594.
Benedict et al., (2009) Colonisation and mass rearing: learning from others. Malar J 8 Suppl 2(Suppl 2): S4.
Benelli et al., (2016) Biological Control of Mosquito Vectors: Past, Present, and Future. Insects 7(4): 52.

(Continued)

*Primary Examiner* — Monica L Perry
*Assistant Examiner* — Brittany A Lowery
(74) *Attorney, Agent, or Firm* — The Roy Gross Law Firm, LLC; Roy Gross

(57) ABSTRACT

The present invention relates to devices and methods for separation of non-adult insects, such as pupae or larvae, according to sexual dimorphisms or developmental stages that can affect their size.

30 Claims, 11 Drawing Sheets

(56) References Cited

OTHER PUBLICATIONS

De Castro Poncio et al., (2021) Novel Sterile Insect Technology Program Results in Suppression of a Field Mosquito Population and Subsequently to Reduced Incidence of Dengue. J Infect Dis 224(6): 1005-1014.
Fay and Morlan (1959) A Mechanical Device for separating the Developmental Stages, Sexes and Species of Mosquitoes. Mosquito News 19(3): 144-147.
Hadinegoro et al., (2015) Efficacy and Long-Term Safety of a Dengue Vaccine in Regions of Endemic Disease. N Engl J Med 373(13): 1195-1206.
McCray (1961) A mechanical device for the rapid sexing of *Aedes aegypti* pupae. Journal of Economic Entomology 54(4): 819.
Papathanos et al., (2009) Sex separation strategies: past experience and new approaches. Malaria Journal 8(Suppl 2): S5; 8 pages.
Sharma et al., (1972) A device for the rapid separation of male and female mosquito pupae. Bull World Health Organ 47(3): 429-432.
Shepard et al., (2011) Economic impact of dengue illness in the Americas. Am J Trop Med Hyg 84(2): 200-207.
Wilder-Smith et al., (2019) Dengue. Lancet 393(10169): 350-363.

\* cited by examiner

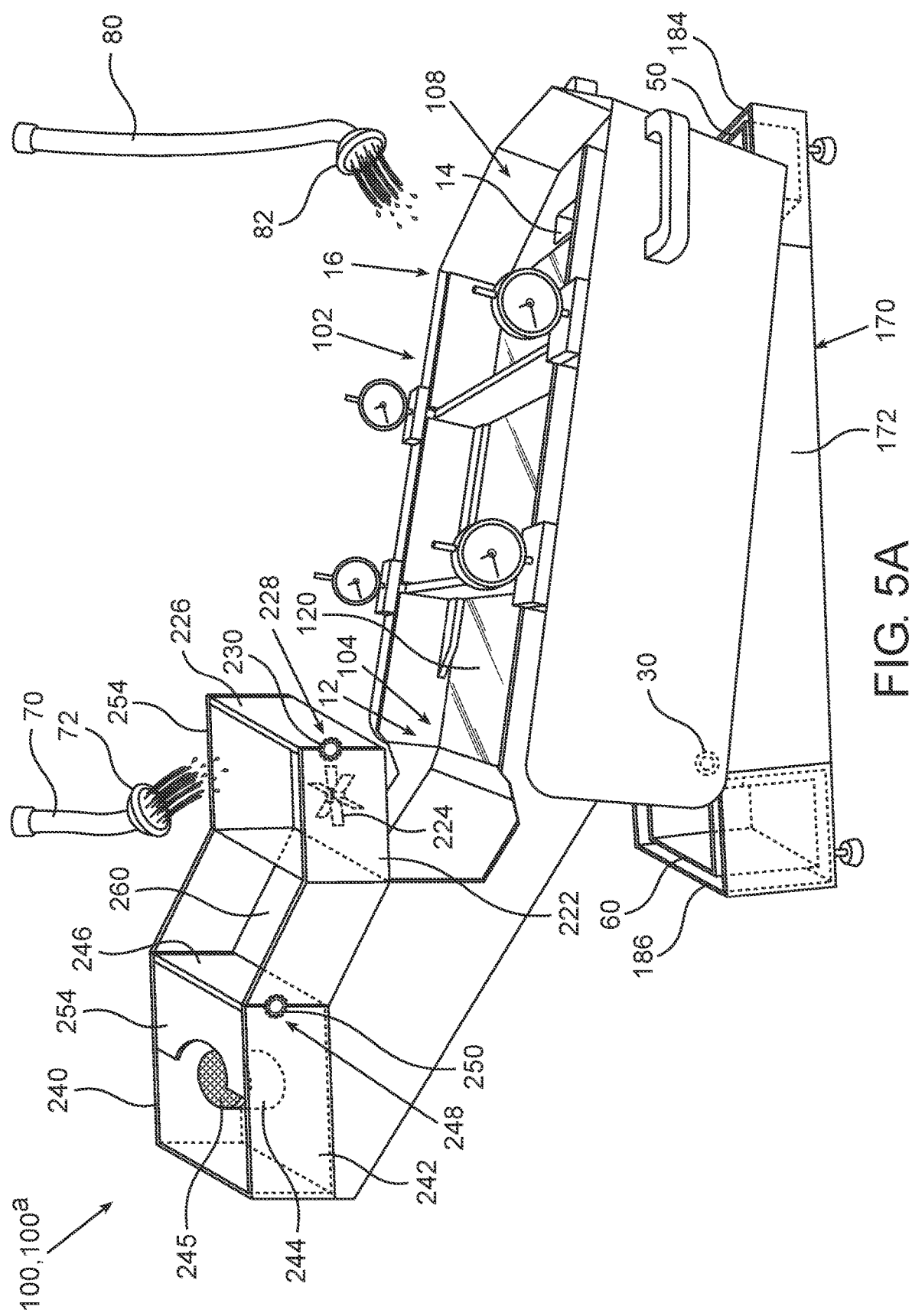

APPARATUS AND METHOD FOR PUPAE SEPARATION

CROSS REFERENCE TO RELATED APPLICATIONS

This application claims the benefit of priority of Israeli Patent Application No. 285542 filed on Aug. 11, 2021, the contents of which are all incorporated herein by reference in their entirety.

FIELD OF THE INVENTION

The present invention relates to devices and methods for separation of non-adult insects, such as pupae or larvae, according to sexual dimorphisms or developmental stages that can affect their size.

BACKGROUND OF THE INVENTION

Sterile Insect Technique (SIT) is a method of disease vector control technique that consists of releasing overwhelming numbers of sterile males. This method has been successfully used for control of human diseases that may be carried by the *Aedes aegypti* mosquito, such as dengue, Zika, and chikungunya. A key challenge is successful implementation of SIT is mass production of sterile males, which requires the implementation of methods and devices that will allow sex separation in a manner which will be reliable, efficient, cost effective and optionally automated, while preserving high quality.

Sexual dimorphism is a widespread trait occurring in many animals and some plants. In certain types of mosquitos, such as *Aedes aegypti*, male pupae are smaller than female pupae. Several solutions have been previously developed for separation of males and females based on sexual dimorphism at the pupal stage. The most common device is the Fay-Morlan glass separator, first described in Fay RW, Morlan HB (1959) "A mechanical device for separating the developmental stages, sexes, and species of mosquitos", *Mosq News* 19, pp. 144-147, which includes two roughly parallel glass plates defining a tapering space therebetween. The distance between the upper and lower portions of the plates, defining the profile of the space, can be manually adjusted with four control knobs.

In use, the contents of a rearing pan are poured from above into the space, and the knobs are manually rotated to adjust the space between the plates such that smaller male pupae may be captured in a lower portion of this space, while female pupae will be captured in an upper portion. The knobs can then be utilized to increase the space at the lower end to allow the male pupae to be flushed into a collecting pan, while female pupae remain trapped between the plates. A separate pan can be placed afterwards below the plates and the space can be further increased to flush away the female pupae for the next batch, requiring the space to be narrowed again and re-adjusted manually in real time during utilization with the subsequent batch. This procedure is labor-intensive and is thus utilized mainly for research. Moreover, repeatability of this procedure is limited since the knobs are opened and closed in each use manually, such that the upper and/or lower space, including the angle of the tapering space from top to bottom, depend on operator's decision and skill and thus may be different in each use. Relying on the operator's skills results in inconsistencies which constitute a major impediment for reliable and repeatable commercial utilization.

Another device is the McCray separator, first described in McCray E M (1961) "A mechanical device for the rapid sexing of *Aedes aegypti* pupae", *J Econ Entomol* 54, pp. 819, includes an inclined aluminum sheet stamped with rows of louvered slits, each 1" long (17 per linear inch) with an opening of 0.039". The screen is attached to a wooden frame that in turn rests upon an inclined metal sheet. In use, water with pupae mixture is poured on one side of the inclined tray, such that the smaller male pupae are washed through the louvered slits and out of a discharge spout at the opposite end of the tray. The screen is then inverted by hand and the female pupae are washed by an opposite stream of water.

One drawback associated with this device is the fact that the space of the slits is set in advance and cannot be adjusted, making it impractical for use across varying types of insects unless set up very precisely for each species. This is more challenging in cases of batch-to-batch variation within a species, for example due to variation in environmental (e.g., temperature, food, density, etc.) or genetic factors, and most importantly, variation between rearing methodologies, which may require size adjustment between uses and optionally between subsequent batches (even for the same species). Another drawback is that the vertical orientation of the slits requires a large amount of water to be poured to pass through the entire height of the slits (1" in the case described by McCray) to fully utilize the entire available area through which the smaller pupae may pass. Finally, the device described by McCray provides a method for rinsing between batches by manually inverting the screen, which again may be labor-intensive and require physical effort of the user after each separation cycle, making it harder to scale up this device and method.

A major key factor for industrial applicability of a separation device is ease of use and reduction of efforts required from the user, as well as significant reduction of overall procedural time, especially when used repeatedly for several batches. The amount of pupae or larvae within a single batch (being poured from a single pan for example) may be sufficient for research facilities. However, for industrial implementation, a volume of water (or other liquid mixture) containing a significantly larger number pupae or larvae is required for the separation procedure. This can be divided into a relatively larger number of pans (or other containers), the contents of which need to be repeatedly poured into a separation device, wherein the larger female pupae, for example, need to be flushed repeatedly between batches. Thus, reduction in man-power and increasing procedural speed, while ensuring batch consistency and performance, are pivot considerations for a design that will allow significant scaling and commercial use.

While some of the previously disclosed devices, described hereinabove, may suffice for a single batch or a small number of batches, such as during experimental set-ups, the effort and time required to flush the female pupae that remain in the device, followed by the need to re-adjust and re-calibrate the devices for subsequent utilization, render them impractical for large-scale, repetitive ongoing industrial utilization. For example, rotating several knobs to enlarge the space between plates of the Fay-Morlan separator, through which female pupae can be flushed, and then rotating the knobs to restrict this passage, requiring real-time fine-adjustment of this space as the subsequent batch is poured, is a tedious and time-consuming process. Similarly, manual inversion of the entire McCray separator so as to flush away the female pupae that did not pass through the louvered slits may require physical force that depends on the weight of the whole device and the rinsing water poured thereon, which can be tiresome after a limited number of repetitive cycles. These types of solution are highly dependent on human factors, such as the operator's skills, experience, patience, wakefulness, etc., which may often result in procedural inconsistencies or even failures. Thus, there is a need for a device that will allow separation of pupae in a robust, reliable, repeatable, consistent, cost effective and scalable manner, which is easily operable and independent of human variability.

SUMMARY OF THE INVENTION

The present disclosure is directed toward devices and methods for sex separation between pre-adult insects.

In one representative embodiment, a separation apparatus is provided. The separation apparatus can comprise a support base, an inclinable tub pivotably coupled to the support base about a pivot axis, and at least one extensible member. The inclinable tube can comprise a rear portion defining a rear flow space, a front portion defining a front outflow space, two tub sidewalls extending between the rear portion and the front portion, at least one adjustable bar extending between the tub sidewalls, and a bar positioning assembly. The at least one adjustable bar defines a gap having a gap height between a lower edge of the adjustable bar and the flow surface. The bar positioning assembly is configured to increase or decrease the gap height by adjusting the position of the adjustable bar relative to the flow surface. The at least one extensible member can comprise a member upper end coupled to the inclinable tub, and a member lower end coupled to the support base. The inclinable tub can be movable between a front-downward inclination of the flow surface, defining a positive inclination angle $\alpha$ between a horizontal plane and the flow surface, and a front-upward inclination of the flow surface, defining a negative inclination angle R between a horizontal plane and the flow surface.

In another representative embodiment, a method for separating non-adult insects is provided. The method can comprise supplying a mixture of fluid and non-adult insects to a rear portion of an inclinable tub while the inclinable tub is in a front-downward inclination of a flow surface thereof, such that the fluid with non-adult insects is urged to flow over the flow surface from a rear portion of the inclinable tub, through at least one gap formed by at least one adjustable bar of the inclinable tub, toward a front portion of the inclinable tub. The method can further comprise collecting the fluid with non-adult insects that passed through the at least one gap and out of the inclinable tub, through a front outflow space of the inclinable tub. The method can further comprise utilizing at least one extensible member for rotating the inclinable tub about a pivot axis to a front upward inclination of the flow surface. The method can further comprise pouring rinse water through a front inflow space of the inclinable tub.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the invention will become more apparent from the following detailed description, which proceeds with reference to the accompanying figures.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures:

FIG. 5A shows another embodiment of a separation apparatus.

DETAILED DESCRIPTION OF SOME EMBODIMENTS

Figure 1A:
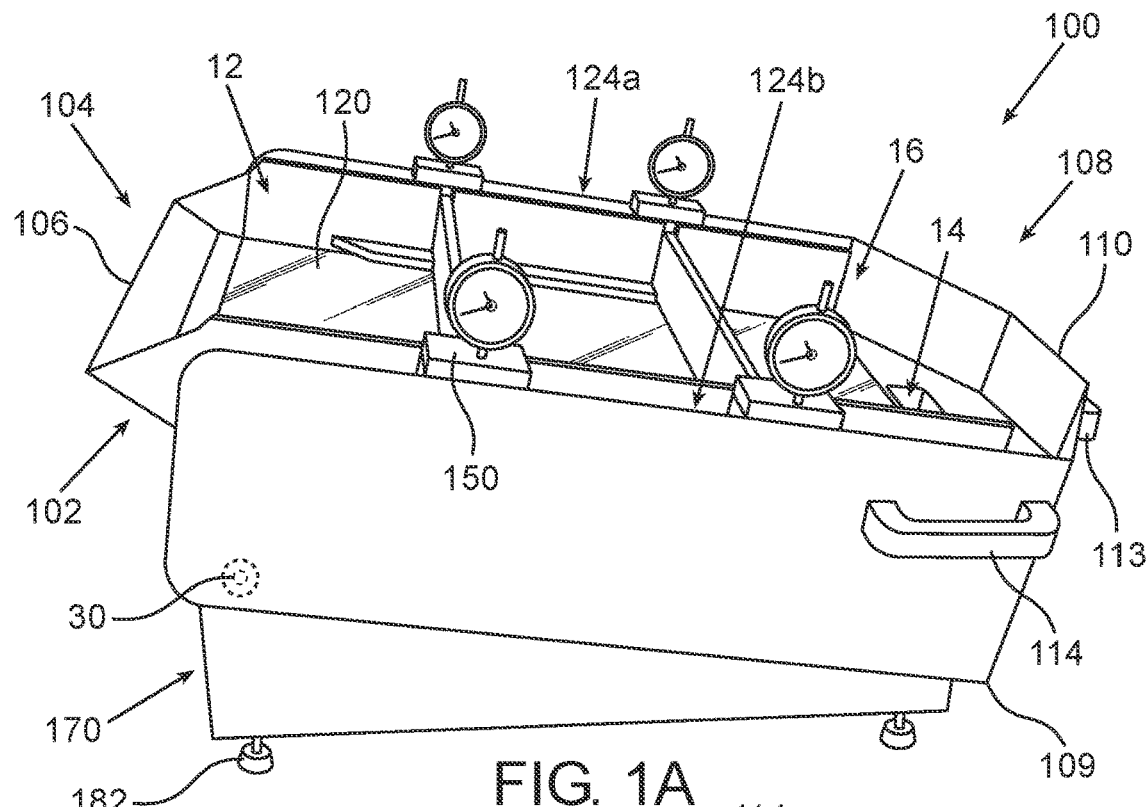
FIG. 1A shows a top-side view in perspective of a separation apparatus, according to some embodiments.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present, or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used herein, the term "integrally formed" refers to a construction that does not include any welds, fasteners, or other means for securing separately formed pieces of material to each other.

As used herein, operations that occur "simultaneously" or "concurrently" occur generally at the same time as one another, although delays in the occurrence of operation relative to the other are expressly within the scope of the above terms, absent specific contrary language.

As used in this application and in the claims, the singular forms "a," "an," and "the" include the plural forms unless the context clearly dictates otherwise. Additionally, the terms "have" or "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language. As used herein, "and/or" means "and" or "or," as well as "and" and "or".

Directions and other relative references may be used to facilitate discussion of the drawings and principles herein, but are not intended to be limiting. For example, certain terms may be used such as "inner," "outer," "upper," "lower," "inside," "outside,", "top," "bottom," "interior," "exterior," "left," right," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same.

Throughout the figures of the drawings, different superscripts for the same reference numerals are used to denote different embodiments of the same elements. Embodiments of the disclosed devices and systems may include any combination of different embodiments of the same elements. Specifically, any reference to an element without a superscript may refer to any alternative embodiment of the same element denoted with a superscript. In order to avoid undue clutter from having too many reference numbers and lead lines on a particular drawing, some components will be introduced via one or more drawings and not explicitly identified in every subsequent drawing that contains that component.

Figure 1B:
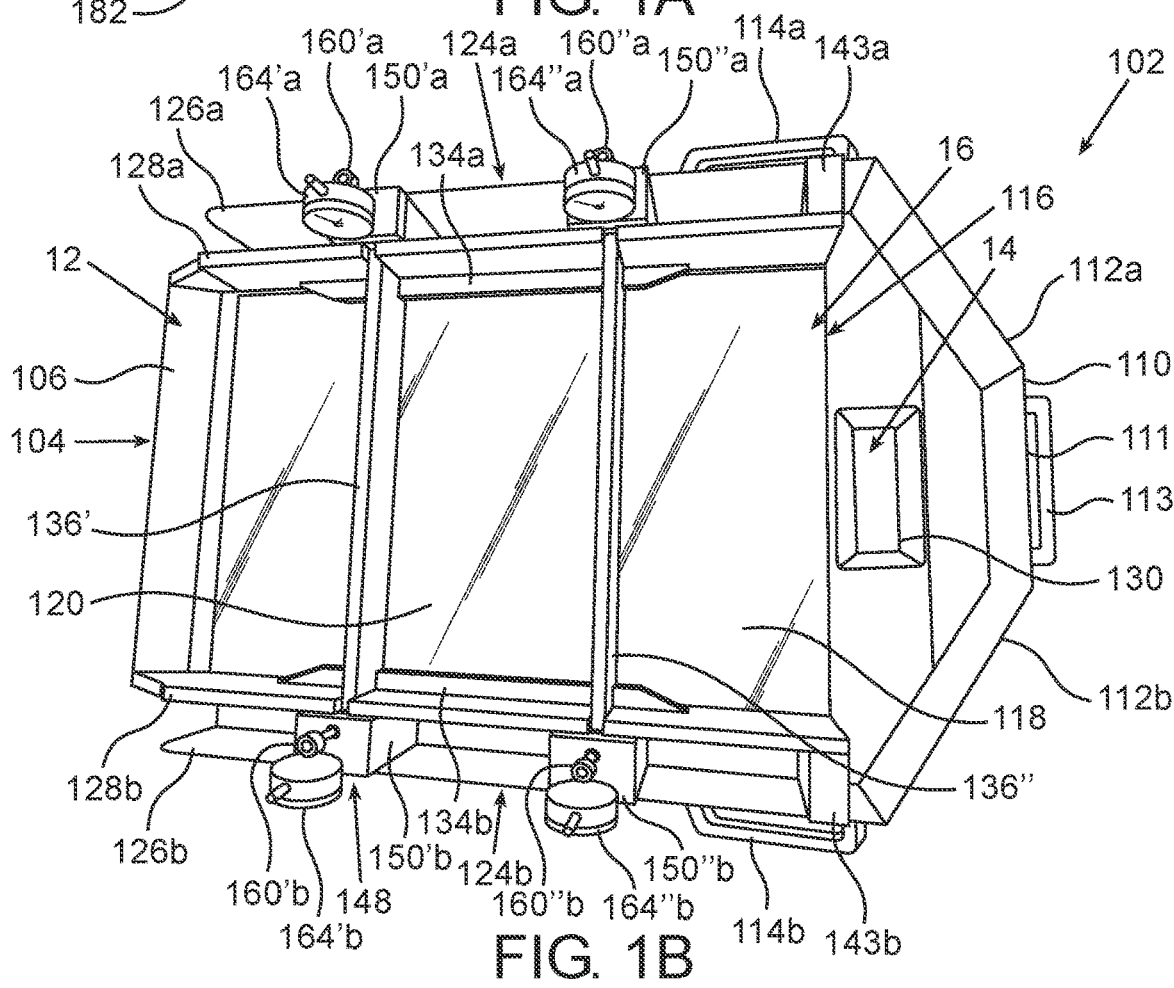
FIG. 1B shows a top view of the separation apparatus of FIG. 1A.
Figure 1C:
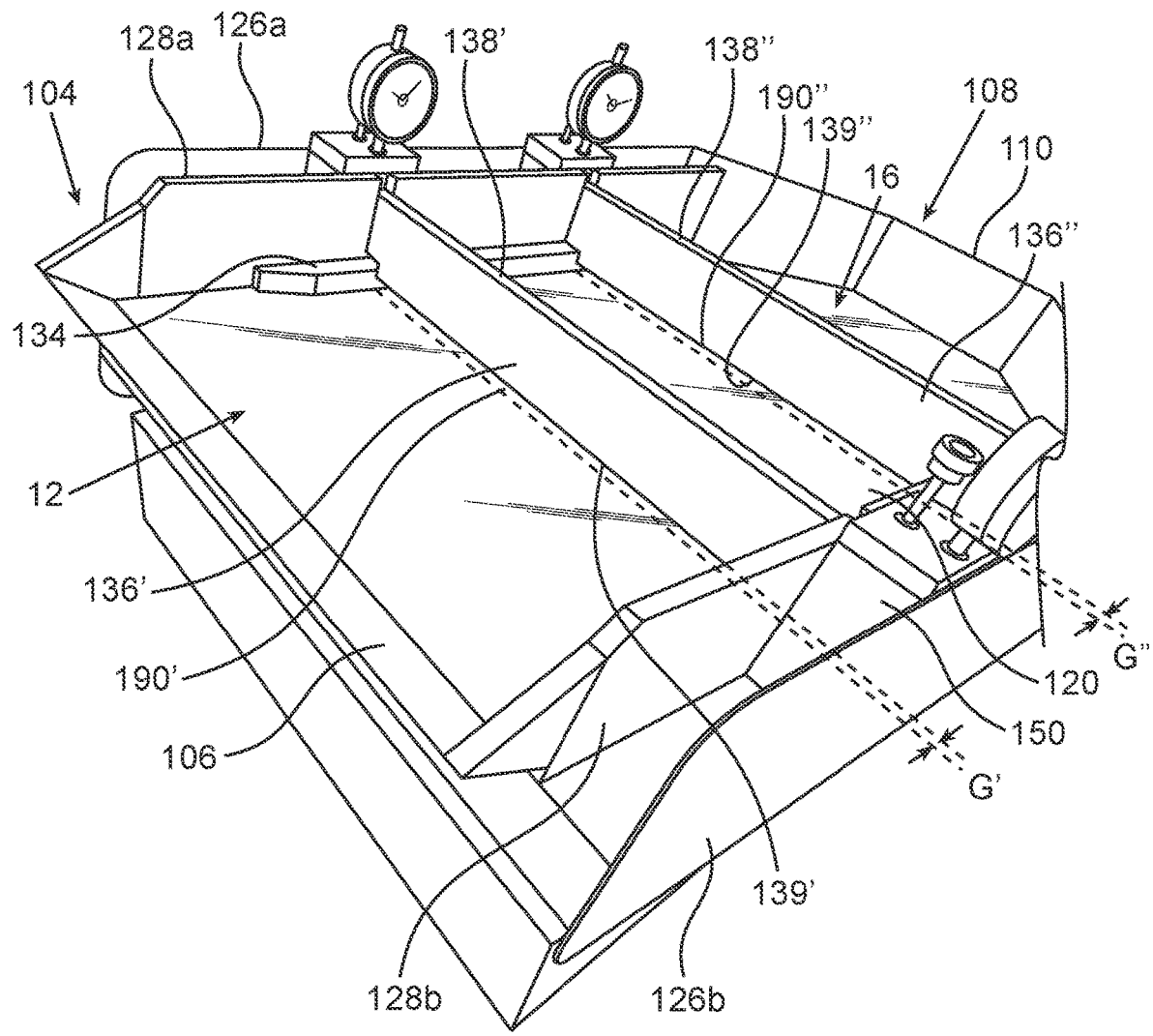
FIG. 1C shows a rear-side view in perspective of the separation apparatus of FIG. 1A.
Figure 2A:
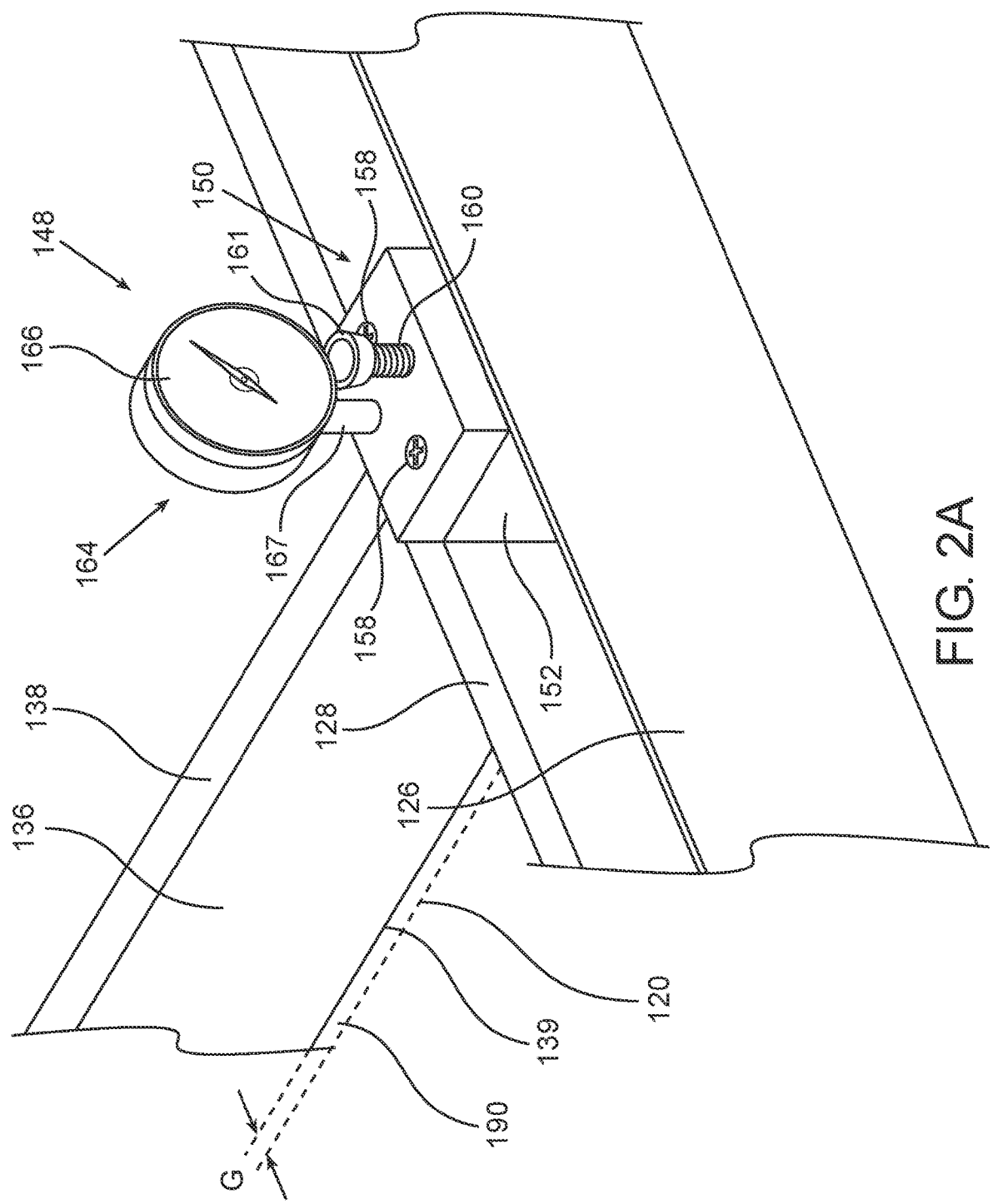
FIGS. 2A and 2B shows a view and a partially exploded view of the separation apparatus, according to some embodiments.
Figure 2B:
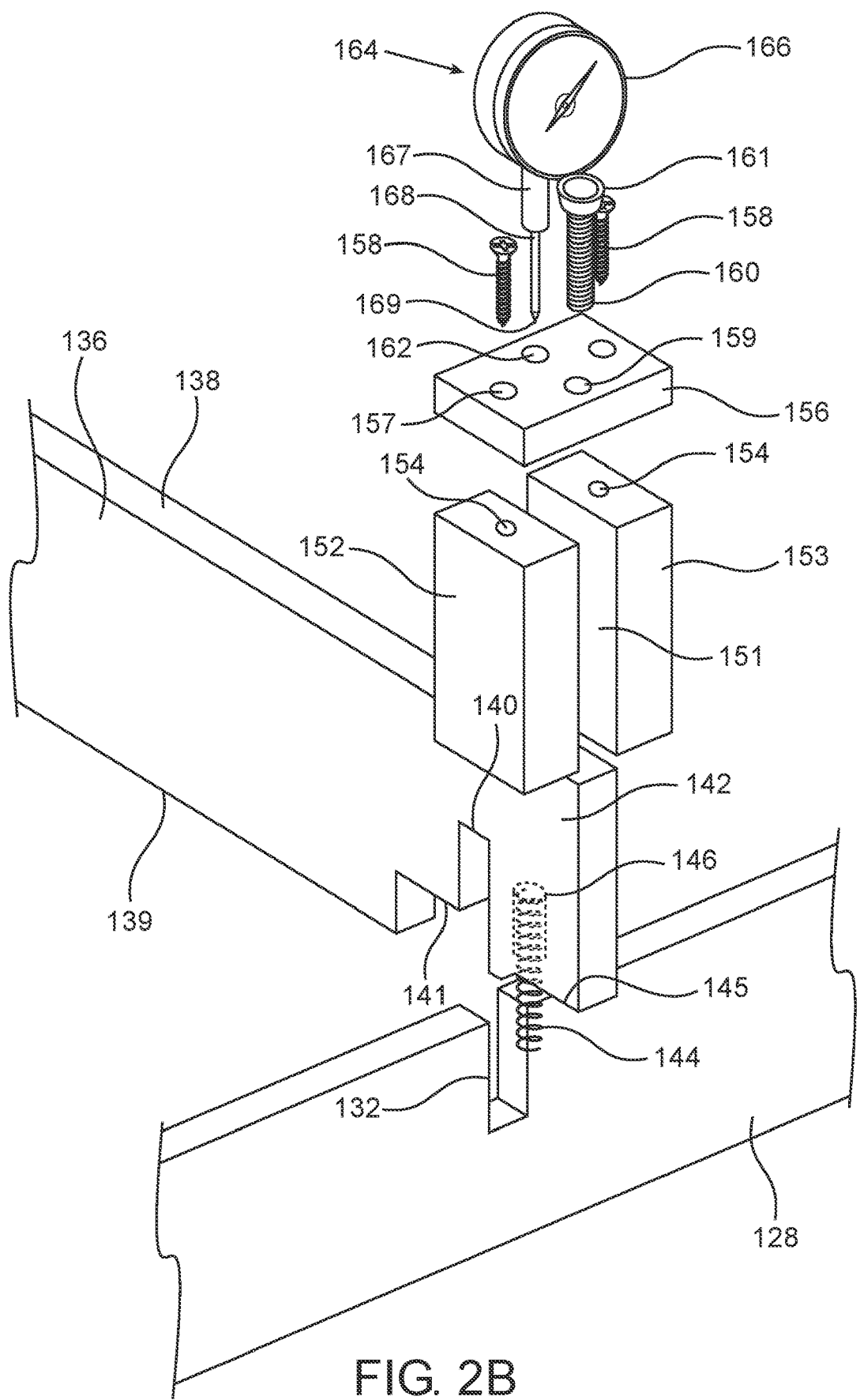
Figure 3B:
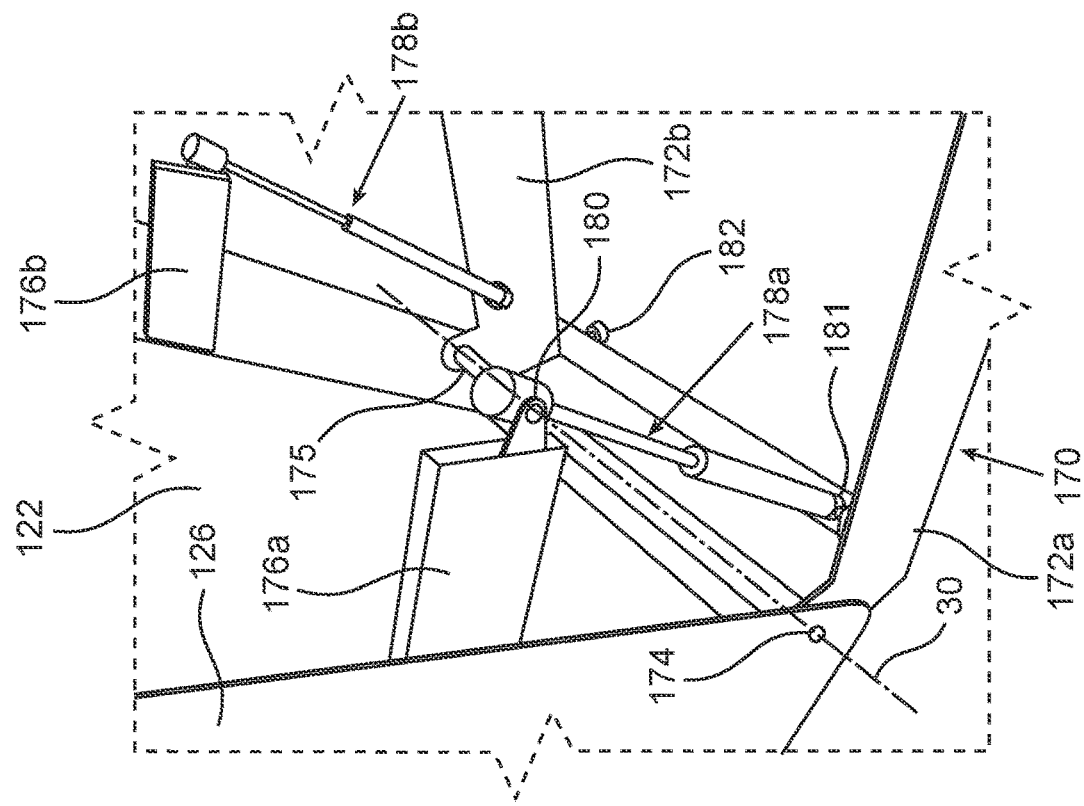
FIG. 3B shows a bottom-side view of the separation apparatus of FIG. 3A.
Figure 3A:
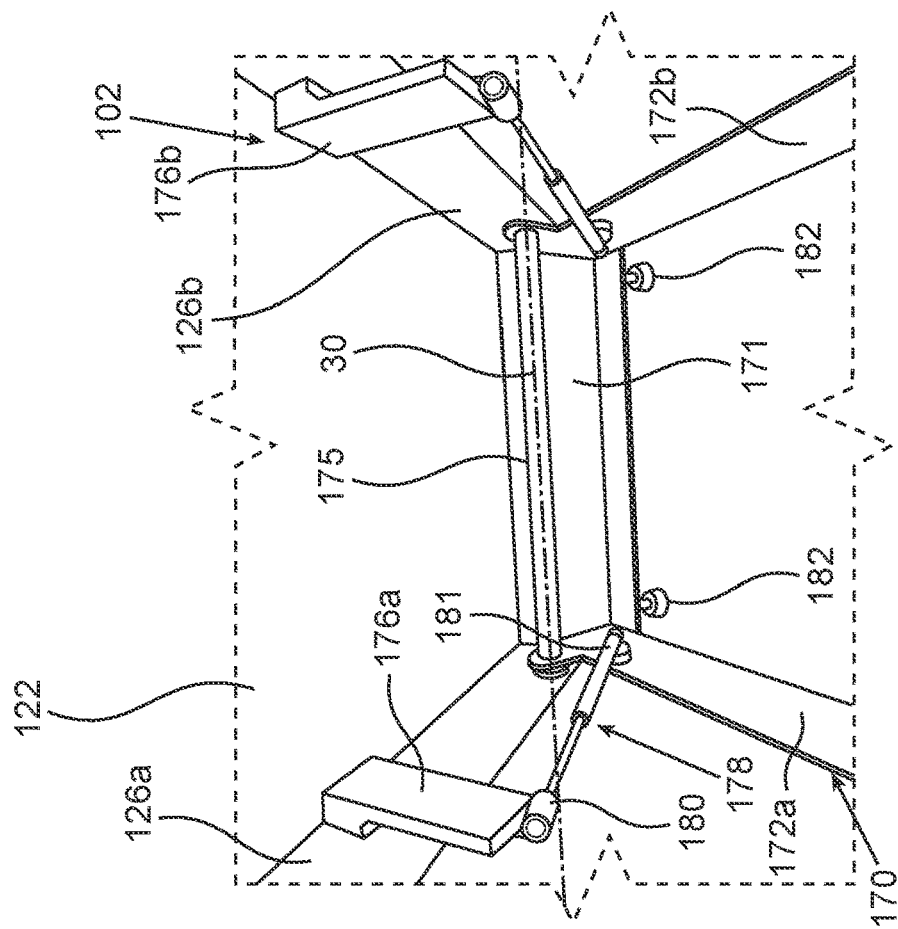
FIG. 3A shows a bottom-front view of a separation apparatus, according to some embodiments.
Figure 4A:
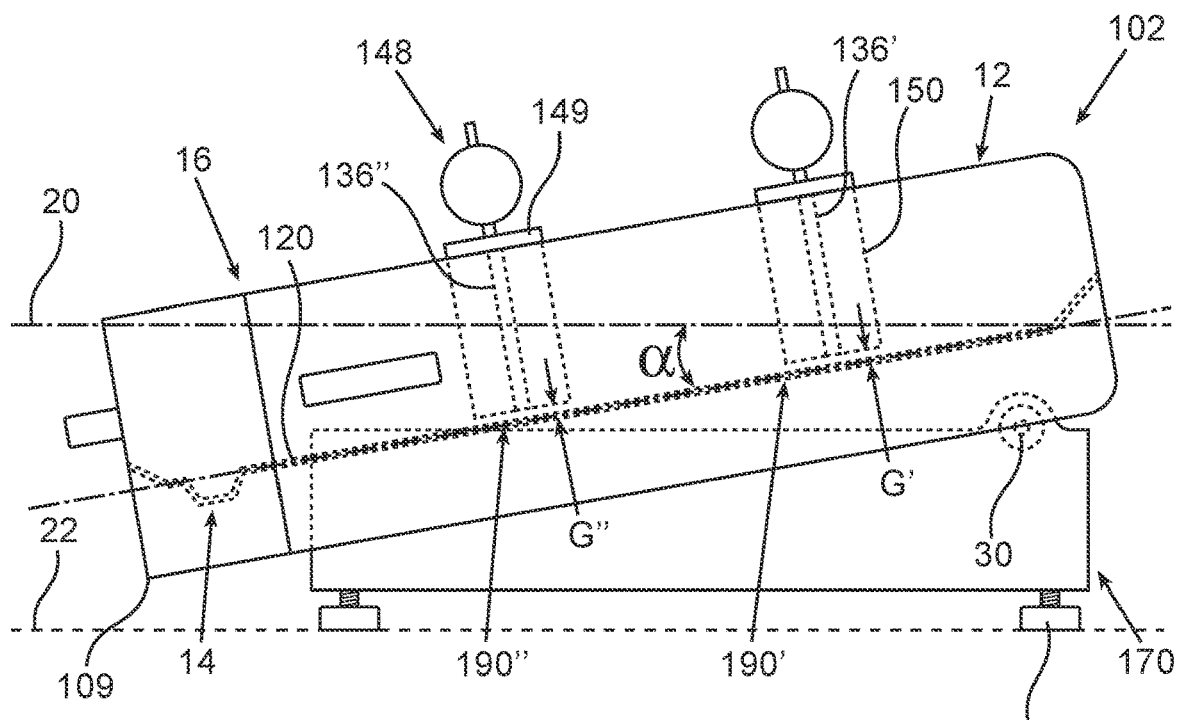
FIG. 4A shows a side view of a separation apparatus in a front-downward inclination, according to some embodiments.
Figure 4B:
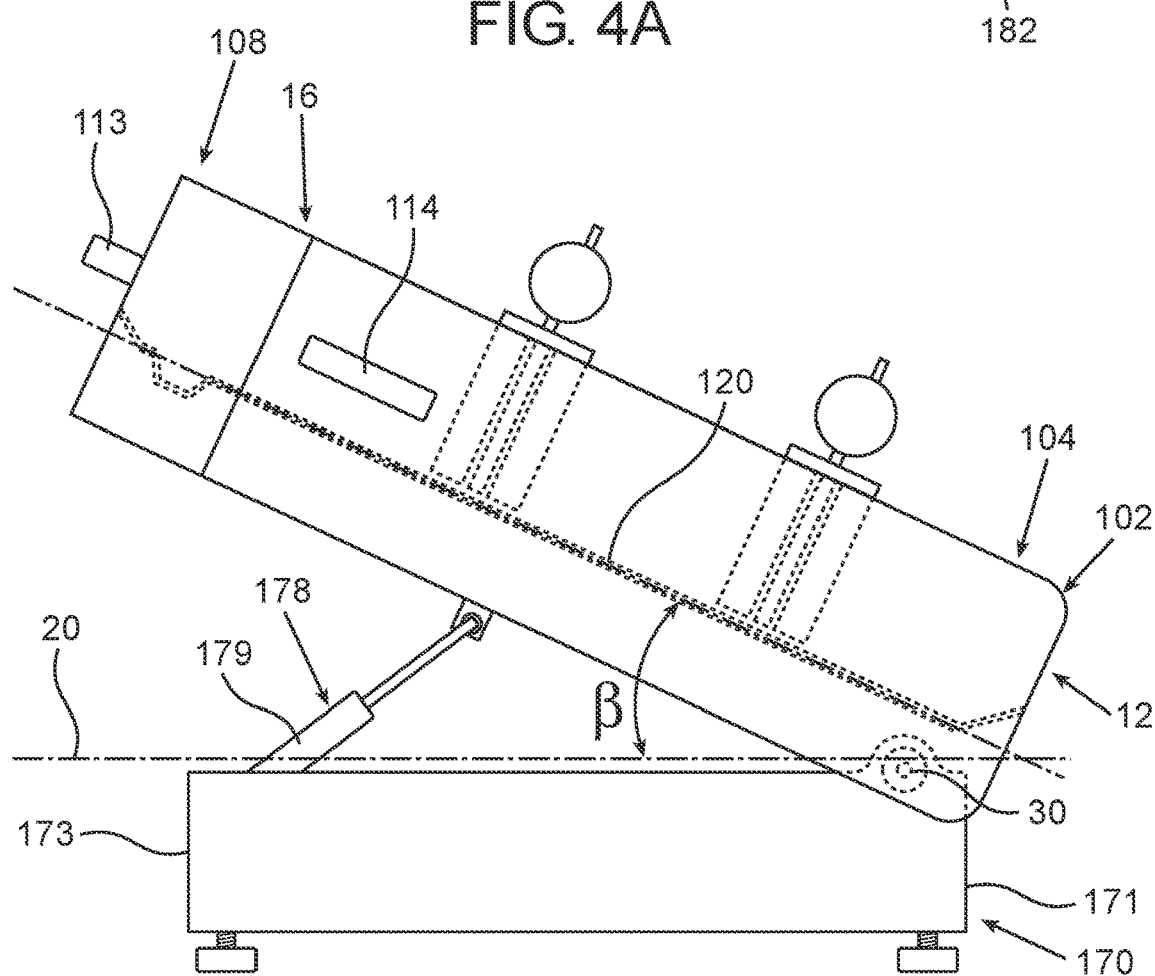
FIG. 4B shows a side view of the separation apparatus of FIG. 4A in a front-upward inclination.

FIGS. 1A, 1B and 1C shows a top-side view in perspective, a top view, and a top-rear view in perspective of a separation apparatus 100 in a front-downward inclination, according to some embodiments. FIGS. 2A-2B show a view and a partially exploded view of the separation apparatus 100 of FIGS. 1A-C. FIGS. 3A and 3B show a bottom-front view and a bottom-side view of a separation apparatus 100 in a front-upward inclination, according to some embodiments. FIGS. 4A and 4B show side views of the separation apparatus 100 of FIGS. 1A-C in a front-downward inclination and in a front-upward inclination, respectively.

The separation apparatus 100 comprises an inclinable tub 102 pivotably coupled to a support base 170 about a pivot axis 30, and at least one extensible member 178 disposed between the support base 170 and inclinable tub 102, operable to adjust the angular orientation of the inclinable tub 102 relative to the support base 170.

The inclinable tub 102 comprises a tub floor 116 defining a flow surface 120, a rear portion 104 defining a rear flow space 12, a front portion 108 defining a front outflow space 14, two tub sidewalls 124 extending between the rear portion 104 and the front portion 108, at least one adjustable bar 136 extending between the tub sidewalls 124 and defining a gap 190 between the adjustable bar 136 and the flow surface 120 of tub floor 116. The inclinable tub 102 further comprises a bar positioning assembly 148 configured to increase or decrease the height G of the gap 190 by adjusting the position of the bar 136 relative to the flow surface 120.

In use, water with pre-adult insects such as pupae of different sizes, which can include larger female pupae and smaller male pupae, can be poured or otherwise streamed, via the rear flow space 12 of the rear portion 104, on or toward the tub floor 116. The flow surface 120 is in a front-downward inclination, meaning that it has a downward inclination toward the front portion 108, to facilitate flow over this surface toward the front portion 108. This can be referred to as the pupae streaming stage in a method of utilizing separation apparatus 100, or more generally as the pre-adult insects streaming stage.

The term "pre-adult insects", as used herein, refers to immature developmental stages, preferably during which the insects are relatively stationary such that they do not move or barely move, such as larvae and/or pupae. It is to be noted that pupae may move in response to environmental conditions, such as light vs. dark environments.

It is to be understood that any reference to a mixture of water with pre-adult insects, such as larvae or pupae, throughout the current specification, may similarly refer to any other suitable fluid or liquid media or solution, such as isotonic aqueous solution and the like.

In the pupae streaming stage, the inclinable tub 102 is inclined such that the flow surface 120, which is the upward facing surface of the tub floor 116, is in the front-downward inclination such that the front portion 108 is lower than rear portion 104, allowing water (or other fluid or mixture) poured thereon to flow thereover toward the front portion 108. Since gravitational forces facilitate flow of water over the flow surface 120 in an inclined orientation thereof, the angle of inclination can be measured relative to the ground. A horizontal plane 20 can be defined as the plane of the ground (or any plane parallel to the ground). A positive inclination angle α can be defined between the horizontal plane 20 and the flow surface 120, as shown in FIG. 4A for example.

The gap 190 defines a positive height G in a direction perpendicular to the flow surface 120, as shown for example in FIGS. 1C, 2A and 4A. The water mixture flows over the flow surface 120 in a forward direction, defined as the direction from the rear portion 104 to the front portion 108, such that the height G of gap 190 is perpendicular to the direction of flow.

As the water mixture flows through the gap 190 defined by the at least one adjustable bar 136, pupae having a size smaller than the height of the gap G may flow and pass therethrough, while pupae having a size larger than the height of the gap G will accumulate against the bar 136 and will not be able to pass through. The smaller pupae that did pass through the gap 190 of the at least one bar 136, or through all gaps of all bars 136 in the case of a tub 102 provided with a plurality of adjustable bars 136, will flow toward and out of the front outflow space 14, for example into a front pan 50 (see FIGS. 5A and 6) that can be placed beneath the front outflow space.

While the procedure of separation is described throughout the current specification with reference to pupae passing through gaps G, it is to be understood that it is similarly applicable to any other pre-adult insects, such as larvae and/or mixture that includes both pupae and larvae.

The flow surface 120 is preferably a planar smooth surface with a low coefficient of friction, to provide a laminar or otherwise undisturbed flow thereover. In some embodiments, the tub floor 116 comprises a glass layer 118 defining the flow surface 120. In other embodiments, the tub floor 116 can be coated by other suitable low-friction materials that define the flow surface.

In some embodiments, the front portion 108 comprises a front wall 110, which can continuously extend from the tub sidewalls 124. In some embodiments, the front wall 110 can define a continuous wall extending between both tub sidewalls 124. For example, in the illustrated embodiment, front wall 110 includes two angled front wall sections 112, continuously extending at an angle from both corresponding tub sidewalls 124 toward each other, and a lateral wall section 111 extending therebetween, which can be substantially parallel to the at least one adjustable bar 136. The angled/convergence of the wall sections 112 toward each other in the front direction can advantageously create a funnel-like configuration, direction the flow toward a front outflow space 14 that can be relatively narrower than the distance between tub sidewalls 124.

In some implementations, the inclinable tub 102 can include other configurations of front walls 110. For example, two angled wall sections, similar to front wall sections 112, can converge at their front ends forming an arrowhead shape without an otherwise oriented lateral wall section therebetween. Alternatively, the front wall 110 can include a single lateral wall section extending all the way from one end of one tub sidewall to the other, without additional angled wall sections. In other alternative configurations, the front wall 110 can have other shapes, such as an arcuate (e.g., half-circular) wall extending between the front ends of the tub sidewalls. In further alternatives, the front portion 108 may be devoid of a front wall, such that the front ends of sidewalls 124 can define an open space therebetween.

The front outflow space 14 is defined as the space/opening through which water and/or pupae may pour out of the inclinable tub 102 when flow surface 120 has a downward inclination toward the front portion 108. In some embodiments, the inclinable tub 102 comprises a front floor opening 130 extending through the tub floor 116 in the region of the front portion 108. In use, a front pan 50 can be placed under the front outflow space 14, for example under the front floor opening 130, such that the water and pupae may be poured therefrom into the pan 50. While a rectangular front floor opening 130 is illustrated in FIG. 1B, it is to be understood that any other shape is contemplated, such as circular, elliptical, trapezoidal, triangular, and the like.

As mentioned hereinabove, the lateral length of the front outflow space 14, including that of the front floor opening 130 when implemented as such, may be shorter, in some implementations, than the distance defined between sidewalls 124 or the lateral length of the gap 190. In such cases, a spout-like configuration of the front wall 110, such as that provided by angled front wall section 112, can advantageously direct the flow with the filtered pupae toward the shorter front outflow space 14. The lateral length of the front outflow space 14 may be dictated by the dimensions of a front pan 50 that can be used in combination with the separation apparatus 100, while the lateral length of the relatively narrow gap 190 can be longer to allow a larger portion of water with pupae pass therethrough.

In some implementations, the front portion 108 may be devoid of a front floor opening 130, and rather define the front outflow space 14 above the edge at the front end of the tub floor 116, for example in front of the adjustable bar 136. For example, the front wall 110 can define a front opening or slot, preferably extending from the front edge of the tub floor 116, serving as the front outflow space 14. In some embodiments, the inclinable tub 102 include angled front wall sections 112 terminating at front edges that are spaced from each other, and devoid of a lateral wall section therebetween, such that the open space defined between the front edges of the angled front wall sections 112 can serve as the front outflow space 14. In yet other embodiment, the front portion 108 may be devoid of a front wall altogether, such that the space between the front edges of both tub sidewalls 124 can serve as the front outflow space 14.

In some embodiments, rear portion 104 comprises a rear wall 106. The rear wall 106 can be inclined relative to the flow surface 120, as shown in the illustrated embodiment, to facilitate flow of water that may be poured thereon toward the gap 190 of the adjustable bar 136. In alternative embodiments, the rear wall 106 can be orthogonal flow surface 120, for example—substantially parallel to adjustable bar 136.

The rear flow space 12 is defined as the space through which water with pupae mixture can be poured into the inclinable tub 102 (e.g., during the pupae streaming stage). In some embodiments, as in the illustrated example, rear portion 104 is open ended, such as behind and above rear wall 106, in which case the entire open space defined behind and/or above the rear portion 104 serves as the rear flow space 12.

After collecting the smaller filtered pupae flowing through the front outflow space 14 (i.e., after the pupae streaming stage), the inclinable tub 102 can be inverted to assume an opposite inclination, such that the flow surface 120 assumes a top-upward inclination in which it has an upward inclination toward the front portion 108 (or otherwise stated, a downward inclination toward the rear portion 104). This can be referred to as the inversion stage in a method of utilizing separation apparatus 100.

In this orientation, water may be poured from the front portion 108 into the inclinable tub 102, to wash away the larger female pupae that remained within the chamber and did not pass through the gaps 190, toward the rear portion 104 and out of the rear flow space 12, optionally into a rear pan (see for example FIGS. 5A and 6) that can be placed below the rear portion 104. Pouring water (or any other suitable rinsing liquid) to wash away the pupae that remain in the inclinable tub 102 can be referred to as the rinsing stage in a method of utilizing separation apparatus 100.

In the rinsing stage, the flow surface 120 is in a front-upward inclination such that the front portion 108 is higher than rear portion 104, allowing water poured thereon to flow thereover toward the rear portion 104 of the separation apparatus 100. A negative inclination angle $\beta$ can be defined between the horizontal plane 20 and the flow surface 120, as illustrated for example in FIG. 4B.

As used herein, a positive angle on inclination is measured relative to a horizontal plane 20, when the front portion 108 is pushed downward. Similarly, a negative angle on inclination is measured relative to a horizontal plane 20, when the front portion 108 is pulled upward.

When present, an inclined rear wall 106 can serve to better direct the flow of water and larger female pupae out of the rear portion 104. While in some embodiments, the same rear flow space 12 can serve both for inflow of water with male and female pupae therethrough when the flow surface 120 is in the front-downward inclination, and for outflow or rinse water utilized to wash the female pupae from the tub when the flow surface 120 is in the front-upward inclination, in other embodiments, the rear portion 104 can include two separate spaces, one for inflow (in the pupae streaming stage) and the other for outflow (in the rinsing stage).

For example, the rear portion 104 can include, in some embodiments, a separate rear outflow space, which can be defined by a bottom opening similar to the front floor opening 130, which can serve to better direct the washout of water with female pupae out of the rear portion 104 when required (embodiments not shown). In such embodiments, water with both male and female pupae can be poured from above on a region of the tub floor 116 which is distanced farther away (toward the front of the tub) from such a bottom opening of the rear portion.

Front inflow space of the inclinable tub 102 is defined as the space through which rinse water can be poured into the front portion 108 to wash the female pupae away from the tub 102 when the flow surface 120 is in the front-upward inclination. In the illustrated embodiment, the front portion 108 is open ended from above, such that front inflow space 16 may be defined as the space over and/or in front of the tub floor 116 at region of the front portion 108. When the front portion 108 includes a front floor opening 130 as in the illustrated example, rinse water will be preferably poured on the tub floor 116 at a position which is distanced farther away (toward the rear of the tub) from front floor opening 130.

While front portion 108 can include a front floor opening 130 from which the small pupae may pour out of the tub, and a separate front inflow space 16 through which rinse water may be poured into the tub, as in the illustrated embodiment, in alternative embodiments—the same space can serve both as the front outflow space 14 and the front inflow space 16 (embodiments not shown). For example, the front portion 108 can be devoid of a front floor opening 130, defining instead a space between two angled front wall sections 112 (replacing the lateral wall section), which can serve both as a front outflow space 14 from which male pupae can be poured out of the tub 102 in the front-downward inclination of the flow surface 120, and serve also as the front inflow space 16 through which rinse water can be poured into the rear portion 104 in the front-upward inclination of the flow surface 120.

In the illustrated embodiment, the inclinable tub 102 is shown to be entirely open from above, such that any of the flow spaces, including a rear flow space 12 and a front inflow space 16 can simply constitute specific regions of the open space above the tub's rear portion 104 and front portion 108, respectively. In other embodiments, the tub 102 can include a top cover (not shown) that enclosed a volume within the tub. In such embodiments, the various spaces can be implemented as opening extending through the thickness of any of the walls of the tub at the corresponding read portion 104 or front portion 108.

After all pupae have been washed away from the inclinable tub 102, it can be reoriented angularly to the front-downward inclination, preferably to the same angle α, after which the above-mentioned procedure can be repeated by pouring the contents of the next batch for pupae separation. Setting or reorienting the inclinable tub 102 to the front-downward inclination prior to the pupae streaming stage can be referred to as the setting stage in a method of utilizing separation apparatus 100, while orienting it to the opposite front-upward inclination between the pupae streaming stage and the rinsing stage can be referred to as the inversion stage of the method.

It may be preferable for the flow of water with pupae over the flow surface 120 in its front-downward inclination, to be gentle enough to prevent the pupae from aggregating in a manner that prevents from smaller pupae to pass through appropriate gaps 190 due to the larger size of such aggregates. One of the factors influencing the rate of flow is the positive inclination angle $\alpha$, as larger inclination angles will result in faster flow velocities. Thus, according to some embodiments, the angle $\alpha$ is a sharp angle. According to some embodiments, the angle $\alpha$ is in the range between 5 and 45 degrees. According to some embodiments, the angle $\alpha$ is in the range between 5 and 30 degrees. According to some embodiments, the angle $\alpha$ is in the range between 5 and 15 degrees. A series of experiments performed by the inventors showed that preferable results have been achieved at an inclination angle of about 10 degrees. Thus, according to some embodiments, the angle $\alpha$ is in the range between 8 and 12 degrees.

While in some designs, an obtuse inclination angle $\alpha$ of more than 45 degrees may yield satisfactory results, the greater this angle is, the higher is the risk for formation of aggregates that can be stuck against the bars 136. In comparison, the alternative Fay-Morlan separator described above is conventionally angled at an inclination of more than 45 degrees with respect to the horizontal plane, such as more than 60 degrees, more than 70 degrees, or even more than 80 degrees with respect to the horizontal plane. Such orientations of the surface along which water with pupae may flow are less desirable in the configuration of the currently disclosed separation apparatus 100.

In contrast to the positive inclination angle $\alpha$, it may be preferable for the negative inclination angle $\beta$ to be larger in magnitude (yet in the opposite direction), to facilitate quicker and more effective washout of the larger pupae (or other non-adult insects) from the tub 102. According to some embodiments, the absolute value of the negative inclination angle $\beta$ is at least two times greater than that of the positive inclination angle $\alpha$. According to some embodiments, the absolute value of the negative inclination angle $\beta$ is at least three time greater than that of the positive inclination angle $\alpha$. According to some embodiments, the angle $\alpha$ is in the range between 5 and 45 degrees. According to some embodiments, the angle $\beta$ is in the range between 20 and 50 degrees. According to some embodiments, the angle $\beta$ is in the range between 25 and 35 degrees.

The bar 136 has an upper edge 138 and a lower edge 139, such that the gap 190 is defined between the lower edge 139 and the flow surface 120. The distance between the floe surface 120 and the lower edge 139 of the bar 136 may be referred to as the height G of the gap. The bar 136 may be in the form of an elongated bar extending between the tub sidewalls 124. In some embodiments, the length of the bar (defined along the directions extending between sidewalls 124) is at least an order of magnitude greater than it thickness (defined in the direction from rear portion 104 to front portion 108).

The term "bar 136" and "adjustable bar 136", as used herein, are interchangeable, and refer to a bar with an adjustable position relative to the flow surface 120, wherein changing the bar's position may be performed prior to or after pouring or otherwise streaming water with pupae into the tub 102 ("after" refers to optional readjustment in preparation for a later upcoming cycle), yet the bar 136 remains stationary (i.e., locked in position) during the pupae streaming stage, and preferably during the rinsing stage as well, such that the height G of gap 190 remains unchanged at least during these stages of utilization of the separation apparatus 100.

As noted above, the terms "pupae streaming stage" and "non-adult insects streaming stage), used throughout the specification and the claims, are interchangeable.

A procedure of gap height (G) calibration may be performed prior to utilization of the apparatus 100 for pupae separation, during which one or more test batches, which can be similar to the water and pupae mixtures described above, are poured over the inclinable tub in its front-downward inclination, wherein the position of the adjustable bar 136 can be readjusted, for example—each time defining a different gap height (G) over a series of test batches poured thereon, so as to calibrate the desired gap 190, or series of gaps 190 if more than one adjustable bar 136 are included, to match the desired separation results. A table of gap height values may be prepared according to pupae type and size, for example, after completion of a series of numerous calibration experiments.

Being able to readjust the height G of the gaps is important if the apparatus 100 is to be used for separating different organisms, such as larvae vs. pupae, or pupae of different insects. Moreover, in some occasions—adjustment may be required between series of batches that can vary in size. Preferably, once calibrated, no further utilization of the bar positioning assembly is required, as the adjusted gap height G remains unchanged even when a large number of batches are repeatedly poured into the inclinable tub (including inversion and rinsing of the tub between subsequent batches).

According to some embodiment, the adjustable bar is a height-adjustable bar 136, and the separation apparatus 100 further comprises a bar positioning assembly 148 configured to move the bar in a direction perpendicular to the flow surface 120, either toward the flow surface 120 so as to decrease the height G of the gap 190, or away from the flow surface 120 so as to increase the height G of the gap 190.

According to some embodiments, the adjustable bar 136 is coupled to at least one tub sidewall 124 by at least one mount 150. According to further embodiments, the adjustable bar 136 is coupled to the tub sidewalls 124 on both ends thereof via two corresponding mounts 150. Each mount 150 can be affixed to the corresponding sidewall 124 on one side thereof, while a corresponding lateral end portion 142 of the adjustable bar 136 is movably coupled to the same mount 150 in a manner that allows the bar 136 to move along the mount 150 utilizing a corresponding bar positioning assembly 148, during an optional stage of bar adjustment, and remain stationary when adjustment thereof is no longer required.

In some embodiments, the bar positioning assembly 148 comprises an adjustment bolt 160 engaged with the bar 136 such that rotation of the adjustment bolt 160 in a first rotational direction (such as clockwise or counterclockwise) facilitates movement of the bar 136 in a first direction (i.e., toward or away from the flow surface 120), while rotation of the adjustment bolt 160 in an opposite second rotational direction facilitates movement of the bar 136 in an opposite direction, wherein the bar movement is in a direction which is substantially perpendicular to the flow surface 120.

In some embodiments, the adjustment bolt 160 is provided with an external threading, and extends through a channel or opening 159 having a complementary internal threading, formed within the corresponding mount 150, such that the lower end of the adjustment bolt 160 is pressed against the upper edge 138 of the bar 136, and in some embodiments, the upper edge of the corresponding lateral end portion 142 of the bar 136. A corresponding end portion 142 may be defined as the portion of the adjustable bar 136 that extends into the mount 150.

In this manner, when the adjustment bolt 160 is rotated in a first rotational direction, it can push the bar 136 closer to the flow surface 120. Each adjustment bolt 160 can have a portion of its stem extending out of the mount 150 (for example, upward therefrom), and include a knob 161 at its upper end, wherein the knob 161 can be used by an operator to manually rotate the corresponding adjustment bolt 160 in either desired rotational direction.

In some embodiments, the bar positioning assembly 148 further comprises a biasing member such as a spring 144 pressed between the bar 136 (e.g., the corresponding lateral end portion 142 of the bar 136) and the tub floor 116 or any portion of the mount 150 below the bar 136. The spring 144 is configured to bias the bar 136 (e.g., to bias the corresponding lateral end portion 142) away from the flow surface 120 in the absence of higher counter-forces applied to the bar 136.

In one implementation, a spring 144 can be attached at its upper end to the bar 136, and its lower end positioned below the lower edge of the bar 139 (for example, at the region of the corresponding lateral end portion 142) and in contact with the corresponding region of the tub floor 116 or a corresponding portion of the mount 150, such that the spring is pressed against the bar 136 in a manner that strives to push it upward (i.e., away from the tub floor 116).

In some embodiments, as in the example illustrated in FIG. 2B, the lateral end portion 142 of the bar 136 includes an internal spring channel 146 extending from the lower edge 139 upward, yet termination below the upper edge 138, such that at least a portion of the spring 144 is accommodated within the spring channel 146, having the spring's upper end attached, or otherwise in contact with, the upper end of the channel 146. In other embodiments, the upper end of the spring 144 can be attached to, or otherwise pressed against, the lower edge 139, such that the spring 144 is exposed along its entire length below the lower edge 139 of the bar 136 (embodiments not shown).

In some embodiments, as in the example illustrated in FIG. 2B, the lateral end portion 142 comprises a spring recess 145 along at least a portion of its lower edge 139, which can serve to expose a longer portion of the spring 144 below the bar 136.

The spring constant and other characteristics of the spring 144 can be chosen such that when the adjustment bolt 160 is pressing against the upper edge 138 of the bar 136 from above, the spring 144 is pushing against the bar 136 from the opposite direction (i.e., from below) to prevent the bar 136 from further falling toward the tub floor 116, while the lower end of the adjustment bolt 160 similarly prevents the bar 136 from being pushed further away from the tub floor 116 by the spring 144. As the adjustment bolt 160 is rotated in a second rotational direction, such that the adjustment bolt 160 moves upward (i.e., away from the tub floor 116), the spring 144 serves to push the bar 136 upward in the same direction, away from the tub floor 116, keeping the upper edge 138 pressed against the adjustment bolt 160.

In alternative embodiments, bar positioning assembly 148 can include an adjustment bolt that can be threaded through a channel with an internal thread formed within the bar itself (for example, extending from the upper edge of the lateral end portion), such that rotation of the bolt may facilitate direct movement of the bar toward or away from the tub floor 116 due to the direct threaded engagement between the bolt and the bar's channel (embodiments not shown).

In some embodiments, as illustrated in FIGS. 1A-C, the bar positioning assembly 148 comprises two adjustment bolts 160, optionally with two corresponding spring 144, engaged with each lateral end portion 142 of the bar 136, for example through corresponding mounts 150 on both sides of the bar 136.

According to some embodiments, the bar positioning assembly 148 further comprises at least one gauge indicator, such as a dial indicator 164, engaged with a corresponding bar 136, configured to provide an indication of the height G of gap 190, for example by providing a visual indication of the position (e.g., height) of the bar 136. The gauge indicator 164 can be mounted on the corresponding mount 150. In some embodiments, the bar positioning assembly 148 includes two gauge indicators 164, each configured to provide an indication of the position of a corresponding lateral end portion 142 of the bar 136, which can be independently movable, for example by an adjustment bolt 160 engaged with the respective lateral end portion 142.

In some embodiments, each tub sidewall 124 is a doubled-walled sidewall, comprising an outer sidewall 126 and an inner sidewall 128. In such embodiments, a respective mount 150 can be positioned between the outer sidewall 126 and the inner sidewall 128, optionally serving as a spacer there-between. Each mount 150 in such embodiments can be affixed to both the inner sidewall 128 and outer sidewall 126. While a double-walled configuration of the tub sidewalls 124 is illustrated, it is to be understood that in other embodiments, a single-walled tub sidewall can be utilized, with a corresponding mount 150 affixed thereto.

In double-walled embodiments of tub sidewall 124, the flow is restricted to the region defined between the inner sidewalls 128, such that the gaps 190 extend between inner sidewalls 128 and do not necessarily extend further to the regions bound between inner sidewalls 128 and outer sidewalls 126 (i.e., the region of the lateral end portion 142). Double-walled configuration can be advantageous for concealing the bar positioning assemblies 148, along with mounts 150, to a dry area through which no liquid flows, thereby preventing flow disturbances that can be otherwise attributed to such structures impeding flow in their vicinity, as well as preventing water/liquids from interacting with any movable components and/or electric components (in relevant embodiments) of the bar positioning assemblies 148.

In some embodiments, as shown in FIG. 2A, each inner sidewall 128 can include at least one guide slot 132 extending downward from its upper end, and the adjustable bar 136 can include a corresponding main recess 140 extending upward from its lower edge 139, such that each main recess 140 is placed over a corresponding guide slot 132. The lateral end portions 142 on both sides of the bar 136 can be defined as the portions extending beyond the corresponding main recesses 140 (i.e., into the mount 150, toward outer sidewalls 126).

In some embodiments, as further shown in FIG. 2A, each mount 150 comprises a first mount portion 152 and a second mount portion 153 spaced from each other so as to define a mount slot 151 therebetween. The mount slot 151 is sized and configured to accommodate the corresponding lateral end portion 142 of the bar 136 therein. The mount 150 can further include a mount cover 156 sized to cover both the first and second mount portions 152, 153, and can be affixed to the first and second mount portions 152, 153 by any suitable fasteners, such as coupling bolts 158 that extend through coupling apertures 157 of the mount cover 156 and corresponding internally-threaded coupling bores 154 of the first and second mount portions 152, 153.

The mount cover 156 can further include an internally threaded adjustment bolt opening 159, through which the adjustment bolt 160 can be threaded and extend downward to press against the upper edge 138 of the lateral end portion 142 situated within the mount slot 151. When the lateral end portion 142 is situated within the mount slot 151, its upper edge 138 is preferably lower than the upper end of the first and second mount portions 152, 153, to form sufficient spaced distance between the lateral end portion 142 of the bar 136 and the mount cover 156, along which the lateral end portion 142 can travel toward or away from the tub floor 116 when required, without being restricted by the mount cover 156.

In some embodiments, the gauge indicator is a dial indicator 164 that includes a display portion 166, a stem 167 and a plunger 168 extending downward therefrom, and terminating with a contact point 169 pressed against the upper edge 138 of the lateral end portion 142 situated within the mount slot 151. The mount cover 156 can include an indicator opening 162 to which the stem can be affixed, while the plunger can extend further downward therefrom. The display portion 166 can include a dial (e.g., a needle dial) with scale graduations, or a digital display in the case of digital dial indicators.

In some embodiments, the gauge indicator is a non-visually readable indicator, and can include a linear electrical position transducer, such as a linear variable displacement transformer (LVDT) or other type of linear voltage transformed, as well as an analog or digital potentiometer, configured to provide an electrical signal equivalent to that visually indicated in display portion 166. Such an electrical signal can be used to drive an automatic electrically powered bar positioning assembly, and/or can be transmitted to a reader device external to the separation apparatus 100, such as an external computer or sever, laptop, smartphone, smartwatch, tablet, or any other device that can be communicate over a wire or wirelessly with the gauge indicator (embodiments not shown).

In some embodiments, the inclinable tub 102 includes a plurality of adjustable bars 136 spaced from each other between the rear portion 104 and the front portion 108. In such arrangements, each adjustable bar 136 can define a gap 190 having a different height G, such that the adjustable bar 136 closest to the rear portion 104 defines the highest gap 190, while the adjustable bar 136 closest to the front portion 108 defines the shortest gap 190.

For example, FIGS. 1A-C show an embodiment of an inclinable tub 102 comprising two adjustable bars: first adjustable bar 136' which is closer to the rear end 104, and a subsequent second adjustable bar 136" closer to the front portion 108. It will be appreciated that reference numerals with prime marks (') refer to elements coupled to or associated with first adjustable bar 136', and double prima marks (") refer to like elements coupled to or associated with second adjustable bar 136". It will be further appreciated that reference numerals with the suffix letter "a" and "b" will refer to elements positioned at opposite lateral sides of the tub 102, such as sidewall 124a and sidewall 124b.

Each of the bars 136' and 136" extends between double-walled tub sidewalls 124a and 124b. More specifically, first bar 136' has one side thereof coupled to mount 150'a disposed between outer sidewall 126a and inner sidewall 128a, and a second opposite side coupled to mount 150'b disposed between outer sidewall 126b and inner sidewall 128b. Similarly, second bar 136" has one side thereof coupled to mount 150"a disposed between outer sidewall 126a and inner sidewall 128a, and a second opposite side coupled to mount 150"b disposed between outer sidewall 126b and inner sidewall 128b.

As further shown in the illustrated embodiment and described above, the bar positioning assembly 148 includes an adjustment bolt 160 mounted in each corresponding mount 150, provided with a knob 161 that can be shaped and dimensioned for manually grabbing and rotating the adjustment bolt 160, and a corresponding gauge indicator, such as dial indicator 164, is also shown to be mounted on each corresponding mount 150.

The adjustment bolts 160 on both sides of each bar 136 can be manipulated to adjust the height of each side of each bar 136, such that first gap height G' is greater than second gap height G". In embodiments in which the position of each side of the bar 136, i.e. each lateral end portion 142 of the bar, is adjusted separately by a corresponding adjustment bolt 160, it is preferable to position each lateral end portion 142 at the same level such that the resulting gap 190 will have a uniform height G along its lateral length. The gauge indicators 164 associated with each side of the bar 136 can provide an indication of the level of the corresponding lateral end portion 142, allowing the operator to manipulate both adjustment bolts 160a, 160b to results in a substantially identical level of both sides of the bar 136.

In some embodiments, when two gauge indicators 164 are provided for each adjustable bar 136, both gauge indicators 164 are positioned on the same side of the corresponding adjustment bolts 160. In the illustrated example, dial indicator 164'a is positioned on one side of the adjustment bolt 160'a, closer to the inner sidewall 128a, while the dial indicator 164'b is also positioned on the same side of the adjustment bolt 160'b, this time closer to the outer sidewall 126b. In this manner, both dial indicators 164'a and 164'b are facing the same side, allowing an operator standing on this side of the separation apparatus 100, adjacent outer sidewall 126b for example, to have a clear line of view without any of the bolts 160 concealing any part of the display portions 166 of the corresponding dial indicators 164.

In use, water with pupae mixture is poured into the inclinable tub 102 from the rear flow space 12 (in the front-downward inclination of the tub 102), such that the larger pupae (i.e., larger than the height G' of first gap 190') accumulate against the first adjustable bar 136', while pupae having a size smaller than G' pass therethrough and flow toward second gap 190". Pupae having a size larger than the height G" of the second gap 190" accumulate against the second adjustable bar 136", while pupae having a size smaller than G" (which can correspond to the size of male pupae) pass through toward the front outflow space 14, defined in the illustrated example by front floor opening 130, through which they can pour into a front pan 50 that can be placed there-under.

Advantageously, this configuration has been tested by the inventors and found to result in favorable outcome, compared to a single bar (with a single slot) configuration, as the double-staged pass through the gaps 190', 190" enables a larger number of male pupae to be properly separated from the larger female pupae, with reduced risk of clogging the gap by the larger female pupae that can have a range of sizes, as well as ensuring adequate performance that will allow collection of pupae with different sizes of female specimens. While an inclinable tub 102 with two adjustable bars 136 defining two gaps 190 is shown in the illustrated embodiment, it is to be understood that any other number of adjustable bars 136, each defining a subsequently shorter gap 190, is contemplated, including arrangements with three bars, four bars, and so on.

The converging shape of the front wall 110, shown in the illustrated example to include two angled front wall sections 112a and 112b oriented toward each other in the front direction, can advantageously form a spout-like geometry directing the water with the smaller pupae that passed through all gaps 190, toward a front floor opening 130 that is narrower than the lateral length of the gaps 190 for example. The dimensions of the front floor opening 130, or any other form of front outflow space 14 through which water with pupae may pour from the inclinable tub 102, can be chosen according to the size of front pans 50 used in combination with the separation apparatus 100.

In some embodiments, there is provided a step 134 positioned at the corner of convergence between a tub sidewall 124 and the tub floor 116. More specifically, in the case of double-walled tub sidewalls 124, the step 134 can be positioned at the corner of convergence between an inner sidewall 128 and the flow surface 120 of tub floor 116. The step 134 can be further attached to any of the respective sidewall 124 (such as to inner sidewall 128) and/or tub floor 116 (including, for example, to glass layer 118).

In some embodiments, as shown in FIG. 2A, the adjustable bar 136 further comprises a complementary step recess 141, which can be continuous with main recess 140, yet preferably shorter than main recess 140. FIGS. 1A-C show an embodiments of an inclinable tub 102 that includes steps 134a and 134b positioned over the corners of inner sidewalls 128a and 128b, and each adjustable bar 136 comprising two complementary step recesses 141a and 141b on both sides, respectively.

Adding steps 134 can reduce the likelihood of pupae accumulation at the corners of the gaps 190. The height of the step recess 141 can be shorter than the height of the step 134, wherein the difference in heights can be defined to match a minimal height G for the corresponding gap 190. In this manner, the steps 134 can serve as stoppers that prevent the lower edge 139 from contacting flow surface 120, thus preventing from the bar 136 from completely blocking flow therethrough.

The term "lateral length", as used herein, refers to a dimension extending between tub sidewalls 124a and 124b. In the case of double-walled tub sidewalls, as in the illustrated example, a lateral length of a gap 190 can be defined between inner sidewalls 128a and 128b. In embodiments that include steps 134, a lateral length of gap 190 can be defined between the steps 134a and 134b.

While the illustrated embodiment of the bar positioning assembly 148 is shown to include two adjustment bolts, each configured to adjust the level of each lateral end portion 142 of the corresponding bar 136, it is to be understood that other mechanisms and assemblies are contemplated. In some embodiments, the bar positioning assembly 148 includes a manually operable mechanism, such as the adjustment bolts 160 with knobs 161 as described above and shown in the illustrated embodiment. The bar positioning assembly 148 can include, as also illustrated, two sub-assemblies, positioned on both sides of the bar 136, each configured to separately adjust the position of the corresponding lateral end portion 142 of the respective adjustable bar 136.

In some embodiments, each bar 136 is adjustable by moving, manually or in any other form, a single subassembly of the bar positioning assembly 148. For example, a single adjustment bolt with a single gauge indicator can be rotated in a manner that facilitates movement of the corresponding bar 136 along its entire lateral length, toward or away from flow surface 120. More specifically, the bar positioning assembly 148 can include a single adjustment bolt with an optional knob, which can be position over a mid-section of the upper edge 138 of a corresponding bar, configured to similarly press against the bar 136 at its midpoint, either directly or via another intermediate component that can be used to spread the forces along the upper edge 138 of the bar 136, such that rotation of the adjustment bolt in a first rotational direction can facilitate uniform movement of the entire bar (embodiments not shown).

In some embodiments (not shown), the bar positioning assembly 148 includes an electrically operable mechanism 149, such as one or more actuators operable via a control circuitry. It is noted that electrically operable mechanism 149 is shielded from view in FIG. 4A by the structure of the bar positioning assembly 148. In some embodiments, such an electrically operable mechanism 149 can include one or more motors arranged to linearly translate each bar 136, optionally by turning the above described adjustment bolt 160. In some embodiments, the electrically operable mechanism 149 can be controlled by a user input device, such as a computer, smartphone, tablet or integrated control panel that includes a user interface. The electrically operable mechanism 149 can position each bar 136 responsive to a respective user input at the user interface, where the user can set the desired gap 190 of each bar 136. In some embodiments, the electrically operable mechanism 149 comprises means for measuring the present height of each bar 136 and/or the size of each gap 190. These measuring means can include, without limitation: an optical sensor; and/or an electrical linear displacement sensor, such as an LVDT or capacitive displacement sensor.

The inclinable tub 102 pivotably coupled to a support base 170 about a pivot axis 30 extending in a lateral direction, for example via one or more hinges. In the illustrated example, support base 170 is implemented as a frame that can be defined by four walls: support base rear wall 171, support base sidewalls 172a and 172b, and support base front wall 173. It is to be understood that support base 170 may assume other shapes, such as having only some of the above-mentioned sidewalls, or having a non-rectangular form, including being formed as any type of block, rod, plate and the like, having linear or curvilinear (e.g., arcuate/circular) edges or surfaces.

FIGS. 3A and 3B shows a front view and a side view in perspective, respectively, of the pivotable connection between inclinable tub 102 and support base 170, according to some embodiments. In the illustrated example, the rear portion 104 of inclinable tub 102 is pivotably coupled to the rear portion of support base 170 via axle 175 extending in the lateral direction, defining for example pivot joint 174a between tub sidewall 126a (and more specifically, outer sidewall 126a in the illustrated example) and support base sidewall 172a, and pivot joint 174b between tub sidewall 124b (and more specifically, outer sidewall 126b in the illustrated example) and support base sidewall 172b. In other implementations, other types of pivotable connections can be utilized, such as two hinges—each defining a pivot joint 174, instead of a single continuous axle 175. Moreover, it is to be understood that other regions of the inclinable tub 102 can be pivotably coupled to the support base 170, for example defining the pivot axis 30 at the region of the front portion 108 instead of the rear portion 104 (embodiments not shown).

The term "inclinable", with reference to the tub 102, means that the inclination of the tub 102, and more specifically, the inclination of its flow surface 120, relative to horizontal plane 20, is adjustable, such that flow surface 120 is movable between a front-downward inclination and a front-upward inclination. Changing the inclination of the flow surface 120 can be achieved by changing the inclination of the entire tub 102, such as by applying rotational movement to the tub 102 about pivot axis 30.

In some embodiments, the separation apparatus 100 comprises at least one extensible member 178 disposed between the support base 170 and the inclinable tub 102. The at least one extensible member 178 can be pivotably coupled to the inclinable tub 102 at an upper end 180 thereof (also termed the member upper end), and/or pivotably coupled the support base 170 at a lower end 181 thereof (also termed the member lower end).

While the extensible members in the illustrated example are coupled, directly or indirectly (for example, via brackets or additional intermediate extensions) to the sidewalls of the tub 102 and/or the sidewalls of the support base 170, it is to be understood that any of the member upper ends 180 and/or member lower ends 181 may be coupled to different portions of the tub 102 of support base 170. For example, member upper end 180 can be coupled (e.g., pivotably coupled) to the tub floor 116 (for example, to a bottom surface 122 thereof, which is the surface of the tub floor 116 facing downward). Similarly, member lower end 181 can be coupled (e.g., pivotably coupled) to the support base front wall 173 (embodiments not shown).

In the illustrated embodiment, separation apparatus 100 includes two extensible members 178, namely extensible members 178a and 178b pivotably coupled at member upper ends 180a and 180b to tub sidewalls 124a and 124b (and more specifically, to outer sidewalls 126a and 126b), and at member lower ends 181a and 181b to support base sidewalls 172a and 172b, respectively. While two extensible members 178 are shown in the illustrated embodiments, it is to be understood that any other number of extensible members may be utilized, including a single extensible member or more than two extensible members. Thus, any reference hereinbelow to two extensible members 178 as shown in the illustrated embodiment, will similarly refer to other implementation of a single extensible member, or more than two extensible members.

For example, a single extensible member 178 can be coupled (e.g., pivotably coupled) at the member upper end 180 to the tub floor 116 (e.g., to bottom surface 122 or an extension extending downward therefrom), wherein the point of connection can be positioned laterally at the center, between both tub sidewalls 124, generally at or closer to the rear portion 104. The member lower end 181 can be coupled (e.g., pivotably coupled) in such an example to the center of the support base front wall 173 (i.e., between both support base sidewalls 172), or to a planar floor of the support base, closer to the front end (embodiments not shown).

Rotatable motion of the inclinable tub 102 about pivot axis 30 can be assisted by one or more such extensible members 178. In some embodiments, as shown in the illustrated example, the extensible members 178 are passive (i.e., non-electric), and can be selected from, but are not limited to, gas struts, gas cylinders, gas springs, hydraulic pistons or pneumatic pistons. Such extensible members 178 are sized to counterbalance the weight of the inclinable tub 102, optionally with contents of water and/or pupae or larvae mixture thereon. In this case, the inclinable tub 102 effectively has a "neutral buoyancy" and may rotate about pivot axis 30, clockwise or counterclockwise, in a controlled manner using minimal manual force.

In some embodiments, the inclinable tub 102 comprises at least one handle, such as front handle 113 attached to front wall 110 (such as to lateral wall section 111 in the example illustrated in FIGS. 1A-C), and/or side handles 114 attached to tub sidewalls 124 (such as side handle 114a and 114b attached to outer sidewalls 126a and 126b, respectively). An operator of the separation apparatus 100 can manually grab such a handle (e.g., front handle 113) so as to pull the front portion 108 of inclinable tub 102 upward, to transition it from a front-downward inclination to a front-upward inclination, or to push it downward to transition from a front-upward inclination to a front-downward inclination.

Advantageously, the extensible members 178, such as gas springs or other alternative elements described above, provide assistance in the range of motion of the inclinable tub 102 such that the force required to rotate the tub 102 about pivot axis 30 to change the inclination of flow surface 120 is reduced. According to some embodiments, the extensible members 178 are configured to provide force to aid the operator in rotating the entire tub 102 about pivot axis 30, optionally single-handedly, such as via front handle 113, in a single motion.

In some embodiments, the maximal stroke of the extensible members 178, such as the stroke of gas springs (i.e., the maximal extent to which the piston can extend away from the cylinder) is selected to reach a front-upward inclination of the flow surface 120 at a specific, maximal negative inclination angle R (e.g., minus 30 degrees). This can simplify usability and repeatability by allowing the operator to pull the front portion 108 upward and rotate the tub 102 about pivot axis 30 up to the exact same inclination angle β, when required.

In some embodiments, the extensible members 178 are also configured to retain the tub 102 in a selected inclination, such that when the tub 102 is in the front-upward inclination, for example, it may remain in this position even when the operator releases the handle, allowing the operator to utilize both hands for other required operations, such as pouring rinsing water on the flow surface 120.

In some embodiments, the inclinable tub 102 further comprises at least one offset extension 176, extending downward, for example below the level of support base sidewalls 172, or more precisely, below the lower edges of support base sidewalls 172. In such embodiments, the member upper ends 180 are coupled to offset extensions. FIGS. 3A-B show two offset extensions 176a and 176b attached to and extending downward from, support base sidewalls 172a and 172b, such that member support end 180a and 180b are pivotably coupled to offset extensions 176a and 176b, respectively. The offset extension 176 can serve as stoppers such that when the tub 102 is rotated toward the front-downward inclination, the rotational movement will halt by the lower ends of the offset extensions 176 contacting the surface 22 on which the supporting apparatus 100 is situated, or alternatively, any other lower surface that can be defined by the support base 170 (e.g., a surface that can be defined by adjustable leg levelers 182, as will be elaborated below), such as a floor 22.

The offset extension 176 can be integrally formed with the corresponding walls of the tub 102, or can be otherwise affixed thereto, such as by welding, screwing, riveting and the like. The length of offset extensions 176 can be designed to achieve a desired positive inclination angle α (for example, an angle of about 10 degrees) when the front portion 108 is pushed maximally downward, without requiring fine adjustments to achieve this angle of inclination from the operator's side. Advantageously, this can support simple operability of the separation device 100 in a repeatable manner, such that the tub 102 can transition to the front-downward inclination at the same angle of inclination a with minimal effort.

While the offset extensions 176 in the illustrated example are attached to the support base sidewalls 172 at their upper ends, it is to be understood that the may be attached to other portions of the inclinable tub 102, such as the bottom surface 122 of tub floor 116. While two offset extensions 176 are shown in the illustrated example, having the upper ends 180 of extensible members 178 coupled thereto, it is to be understood that any other number of offset extensions is contemplates, including one or more than two, and that the extensible members are not necessarily coupled to the extensions sidewalls.

For example, the tub 102 can include a single offset extension attached to the front wall (for example, to the lateral wall section 111) and extending downward therefrom, while the upper ends 180 of extensible members 178 can be coupled to support base sidewalls 172 which are devoid of any extensions, such that the bottom end of the single frontal offset extension is similarly dimensioned to serve as a stopper and contact the bottom surface on which the apparatus 100 is situated, resulting in the front-downward inclination with the desired angle α (embodiments not shown).

In yet other embodiments, the tub 102 does not necessarily include separate extensions, but rather has one or more of its walls dimensioned to serve as stoppers with similar functionality. For example, while a front lower edge 109 of the front wall 110 is shown in FIG. 4A to be spaced upward from the bottom/ground surface 22, in other embodiments, the front lower edge 109 of the front wall 110 can be configured to contact the bottom surface 22 when reaching a desired angle α in the front-downward inclination. Thus, in some embodiments, the separation apparatus 100 includes a downward rotational stopping feature, implemented either as at least one offset extension 176 affixed to the tub 102 or as an edge of at least one of the walls of the inclinable tube 102, such as front lower edge 109 of front wall 110, configured to allow front portion 108 of the tub 102 to be pushed downward up to a front-downward inclination of the flow surface 120 at a specific angle of inclination a (e.g., about 10 degrees), and prevent further rotation of the tub 102 in the same direction about pivot axis 30, such that the inclination angle α cannot increase further.

This allows the procedure to be repeatable, such that after utilization of the apparatus 100 for each batch of pupae, after which the remaining larger pupae are washed away therefrom, the tub 102 may assume the exact same position (i.e., the front-downward inclination at the exact same inclination angle α) with minimal effort and without requiring any specific fine adjustments from the operator.

In some embodiments, the support base 170 further comprises one or more adjustable leg levelers 182 fastened to its lower end, such as the four adjustable leg levelers 182 shown in the illustrated embodiment at or near the four corners of the lower end of support base 170. Each adjustable leg leveler 182 can include a threaded section and terminate at a foot or pad designed to rest on the underlying ground or surface 22 (see FIG. 4A). The adjustable leg levelers 182 are configured to increase or decrease the height of the support base 170, and to keep t uniform angle of inclination at every point along the flow surface 120. When placed on a surface 22 substantially parallel to the ground, horizontal plane 20 (or a plane parallel thereto) can be defined as a surface passing through pivot axis 30, and parallel to the ground surface 22 which is defined by the bottom ends of the adjustable leg levelers 182. When placed over an uneven underlying surface 22, the adjustable leg levelers 182 can be employed to align the support base 170, preferably at the level of connection thereof to the member lower ends 181, with a plane parallel to the horizontal plane 20.

In some embodiments, the extensible members 178 are motorized, comprising an electrically operable mechanism 179 arranged to extend and retract the extensible members 178. For example, electro-mechanical actuators or servomotor actuators may be utilized to actuate extensible members 178 that can include, but are not limited to, threaded shafts, telescopic shafts (including hydraulic or pneumatic pistons) or stepped struts. It is noted that electrically operable mechanism 179 is shielded from view in FIG. 4B by the structure of the extensible member 178. In some embodiments, the motorized actuators can be controlled by a user input device, such as a computer, smartphone, tablet or integrated control panel that includes a user interface. The motorized actuators can extend each extensible member 178 responsive to a respective user input at the user interface, where the user can set the desired angle of inclination. Particularly, responsive to the selected angle of inclination, a processor of the user input device, or a dedicated processor or control circuitry, determines the appropriate length to extend the extensible members 178 in order to achieve the selected inclination angle, $\alpha$ or $\beta$, respectively. Means may be provided for latching or locking the inclinable tub 102 in any of its front-downward or rear-downward positions.

As stated above, it may be desirable to control the flow of water mixture that includes non-adult insects poured or streamed into the inclinable tub 102. In some embodiments, such a mixture is contained within an enclosed chamber provided with a movable gate that either defines the rear flow space 12 or defines an opening through which water with non-adult insects may be streamed, through the rear flow space 12, into the tub 102, wherein the gate is movable between a closed state and a variety of open states, such that the degree of opening defined by the gate is set to provide a desired degree of flow into the tub 102.

In some embodiments, the separation apparatus 100 further comprises a flow-control chamber 220 defining an enclosed volume in which water mixture with pupae and/or larvae can be stored, and from which such mixture can be streamed into the rear portion 104 of the tub 102. FIG. 5A shows one embodiment of a separation apparatus 100a that includes a flow-control chamber 220, and FIG. 6 shows another embodiments of a separation apparatus 100b provided with a flow-control chamber 220, wherein the differences between these embodiments will be elaborated in greater detail below.

Flow-control chamber 220 defines a control chamber floor 222, and includes a flow control gate 226 at its front end. The flow control gate 226 is movable toward or away from the control chamber floor 222, between a closed position shown in FIG. 5A, and an open position shown, for example, in FIG. 5C. The flow-control chamber 220 can include a control gate displacement mechanism 228 configured to move the gate 226, and more specifically, the lower edge of the gate 226, toward or away from control chamber floor 222. The control gate displacement mechanism 228 can be implemented as a manual or electrically controlled mechanism. For example, the control gate displacement mechanism 228 can include one or two knobs 230, such as the rotatable knobs 230 illustrated in FIGS. 5A-C, which can be manually grasped to maneuver the position of the flow control gate 226, via known mechanisms such as rack-and-pinion and the like. In general, the control gate displacement mechanism 228 can be implemented in a similar manner to that described for any embodiment of the bar positioning assembly 148, including via adjustment bolts similar to bolts 160, or via electrically controlled actuators 232 as illustrated for example in FIG. 6. As described above in relation to bar positioning assembly 148, in some embodiments, electrically controlled actuators 232 can be controlled by a user input device, such as a computer, smartphone, tablet or integrated control panel that includes a user interface. The electrically controlled actuators 232 can displace gate 226 to switch between the open and closed position.

Water with non-adult insects can be poured or streamed into the flow-control chamber 220 while the flow control gate 226 is in the closed position (closed position of gate 226 shown in FIG. 5A), such that in this position the non-adult insects are retained within the chamber 220. The flow-control chamber 220 is in fluid communication with the rear-portion 104 of the inclinable tub 102, such that when the gate 226 transitions to the open position (such as illustrated, for example, in FIG. 5C), the mixture of water and non-adult insects are streamed through the opening defined between the flow control gate 226 and the control chamber floor 222 toward the tub floor 116 and the adjustable bars 136.

A component which is "in fluid communication with" another component, as used throughout the specifications, means that in the absence of any intervening obstacles (such as a closed gate), liquid can freely flow from the first component into the second component. For example, the flow-control chamber 220 being in fluid communication with the rear portion 104 of inclinable tub 102, means that as long as the gate 226 is in the open position, liquid (e.g., water mixture and the like) can freely flow from the flow-control chamber 220 into the rear portion 104 of inclinable tub 102.

The control chamber floor 222 can be either at the level of the flow surface 120 of the tub 102, or above the flow surface 120. In some embodiments, the flow control gate 226 is positioned at or behind the rear portion 104 of the inclinable tub 102, such that when the gate 226 is in the open position, the rear flow space 12 is defined by the opening between the gate 226 and the control chamber floor 222. In some embodiments, the flow control gate 226 can be positioned at the rear portion 104 of the tub 102, above the tub floor 116, such that in its open position, water with non-adult insects can be poured from the opening defined between the gate 226 and the control chamber floor 222, toward the rear flow space 12 that can be an open (i.e., uncovered) space above the rear portion 104, as in the embodiment illustrated in FIG. 6.

Advantageously, the degree of opening between the flow control gate 226 and the control chamber floor 222 can be adjusted to allow streaming of the water with non-adult insects into the inclinable tub 102 at a desired flow rate, for example by controlling the position of the gate 226 relative to floor 222 via control gate displacement mechanism 228. This is in contrast to alternative implementations of manually pouring water with non-adult insects from a pan or any other container, which can result in undesirable splashes, flow disturbances, and varying non-repeatable procedures that depend solely on the user's talents. As described above, in some embodiments electronically controlled actuators 232 are provided to control the opening and closing of the flow control gate 226. In such an embodiment, responsive to a respective user input received at the user interface indicating a desired position of the gate 226 relative to floor 222, electronically controlled actuators 232 move the flow control gate into the desired position. In some embodiments, gate displacement mechanism 228 comprises means for measuring the position of flow control gate 226 in relation to floor 222. These measuring means can include, without limitation: an optical sensor; and/or an electrical linear displacement sensor, such as an LVDT or capacitive displacement sensor.

In some cases, non-adult insects such as larvae or pupae may tend to stick together and form aggregates that will be larger in size and prevent them from properly passing either through the opening defined by the flow control gate 226 in its open position, or any of the gaps 190. In some embodiments, the flow-control chamber 220 further includes a stirrer 224 that can be implemented as an impeller which is electrically or magnetically rotatable, configured to stir the mixture of water with non-adult insects within the chamber 220. This action breaks up any such aggregates or prevents the non-adult insects to stick to each other to form such aggregates. The material properties, dimensions and shape of the stirrer 224, and its speed of rotation, are configured to avoid any damage that may be caused to the non-adult insects during this action.

As water mixture with non-adult insects flows from the flow-control chamber 220 into the tub 102 in the open position of the gate 226, the level of the water mixture within the chamber 220 may be reduced such that when this level is closer to the control chamber floor 222 (i.e., reduced content of water in the mixture), a portion of the pupae or larvae that remain in the chamber 220 may stick to the control chamber floor 222 rather than flow into tub 102. Adding water (or other suitable fluid) to the chamber 220 during this stage can prevent this phenomena and allow all non-adult insect to properly flow into the tub 102.

In some embodiments, the separation apparatus 100 further comprises an inflow pipe 70 in fluid communication with the flow-control chamber 220, configured to pour additional water into the flow-control chamber 220. The opening of inflow pipe 70, from which water exit the pipe 70, can be positioned above the flow-control chamber 220, oriented to direct the water flowing therefrom into the chamber 220. The term "pipe" is non-limiting, and can include a rigid pipe, a flexible hose, a faucet and the like. In some embodiments, the inflow pipe 70 further includes an inflow sprayer 72 at its end portion, as illustrated for example, in FIG. 5A. In other embodiments, the inflow pipe 70 is open ended without including a sprayer, as illustrated for example in FIG. 6.

While the inclinable tub 102 and the adjustable bars 136 may be utilized to separate non-adult insects according to size, for example for separation of male pupae from female pupae as described above, it may be desirable in some implementation to add a preliminary stage of separation that will separate very large non-adult insects (e.g., larger larvae) from smaller non-adult insects, which are still larger than the final desired size defined by the final (i.e., front-most) gap 190. For example, the initial contents of a mixture with non-adult insects can include both larvae and pupae, wherein larvae generally have different body shape, size, and different in-water behavior, compared to pupae. It may be desirable separate between larvae and pupae prior to streaming them into the tub 102, so as to avoid the larvae, or relatively very large pupae, from accumulating against the adjustable bar 136 in a manner that may clog at least a portion of the gap 190.

In some embodiments, the separation apparatus 100 further comprises a preliminary separation chamber 240 defining an enclosed volume in which water can be stored and in which a bowl 244 with a sieve 245 can be placed, and from which water, preferably with non-adult insects, can be streamed toward and into the flow-control chamber 220. FIG. 5A shows one embodiment of a separation apparatus 100a that includes a preliminary separation chamber 240, and FIG. 6 shows another embodiments of a separation apparatus 100b provided with a preliminary separation chamber 240.

Preliminary separation chamber 240 defines a preliminary chamber floor 242, and includes a preliminary gate 246 at its front end. The preliminary gate 246 is movable toward or away from the preliminary chamber floor 242, between a closed position shown in FIG. 5A, and an open position shown, for example, in FIG. 5B. The preliminary separation chamber 240 can include a preliminary gate displacement mechanism 248 configured to move the gate 246, and more specifically, the lower edge of the gate 246, toward or away from preliminary chamber floor 242. The preliminary gate displacement mechanism 248 can be implemented as a manual or electrically controlled mechanism. For example, the preliminary gate displacement mechanism 248 can include one or two knobs 250, such as the rotatable knobs 250 illustrated in FIGS. 5A-C, which can be manually grasped to maneuver the position of the preliminary gate 246, via known mechanisms such as rack-and-pinion and the like. Similar to control gate displacement mechanism 228, the preliminary gate displacement mechanism 248 can be implemented in a similar manner to that described for any embodiment of the bar positioning assembly 148, including via adjustment bolts similar to bolts 160, or via electrically controlled actuators 252 as illustrated for example in FIG. 6. As described above in relation to electrically controlled actuators 232, in some embodiments, electrically controlled actuators 252 can be controlled by a user input device, such as a computer, smartphone, tablet or integrated control panel that includes a user interface. The electrically controlled actuators 252 can displace the preliminary gate 246 to a desired position in relation to preliminary chamber floor 242.

A bowl 244 that includes unsorted non-adult insects, such as both larvae and pupae spanning a relatively wide range of sizes, can be placed within a volume of water contained in the preliminary separation chamber 240 while the preliminary gate 246 is in the closed position (closed position of gate 246 shown in FIG. 5A), such that in this position the surrounding volume of water (with or without non-adult insects) is retained within the chamber 240. In general, pupae developmental stage is a transitional phase between aquatic and terrestrial phases, which will result in higher dependency of pupae on air at the surface of the water they are contained in, relative to larvae. This will result in increased tendency of pupae to "swim" upward toward the water surface (through sieve 245), while larvae may remain buoyant within the water.

The bowl 244 is formed as a generally enclosed container that include a sieve 245 having a mesh size that will allow non-adult insects smaller than this mesh size to pass through the sieve 245 into the surrounding water, while larger non-adult insects will remain trapped within the bowl 244. For example, the mesh size can be selected to allow only pupae pass therethrough, while retaining larvae within the bowl. The mesh size will be larger than the gap height G of the smallest (i.e., front-most) gap 190, so as to serve for preliminary size separation but not obviating the necessity of utilization of adjustable bars 136 for sex separation. It is to be understood that even in such an example, larvae having a size smaller than the mesh size can still pass into the surrounding water, and pupae having a size larger than the mesh size will stay entrapped within the bowl 244, though due to the different respiratory behavior, larvae will have a decreased tendency to swim and pass through the sieve 245 to begin with, and even if they do reach the sieve 245, the mesh density is set to allow only non-adult insect smaller than the sieve apertures to pass therethrough, and most larvae are larger than pupae. Furthermore, the body of larvae may be shaped differently than that of pupae, for example including bristles that will further compromise their ability to pass through the sieve 245.

The preliminary separation chamber 240 is in fluid communication with the flow-control chamber 220, such that when the gate 246 transitions to the open position (such as illustrated, for example, in FIG. 5B), the mixture of water and non-adult insects that passed thereto through the sieve 245 are streamed through the opening defined between the preliminary gate 246 and the preliminary chamber floor 242 toward the flow-control chamber 220.

In some embodiments, the preliminary separation chamber 240 is spaced away from the flow-control chamber 220, and the separation apparatus 100 further comprises a guide channel 260 extending between the preliminary separation chamber 240 and the flow-control chamber 220, being in fluid communication with both. In such embodiments, when the gate 246 transitions to the open position, the mixture of water and non-adult insects are streamed through the opening defined between the preliminary gate 246 and the preliminary chamber floor 242, through the guide channel 260, into the flow-control chamber 220. In some embodiments, the preliminary chamber floor 242 is also higher than the control chamber floor 222, such that the floor of guide channel 260 is inclined as illustrated throughout FIGS. 5A-6.

In some embodiments, the preliminary separation chamber 240 further comprises a cover 254 extending rearward from the preliminary gate 246, so as to cover a frontal portion of the preliminary separation chamber 240 from above, but not the entirety of the chamber 240. The pupal stage is a resting, non-feeding stage of development, yet pupae may be mobile and respond to light changes, swimming in a tumbling action toward darker regions in the water. The role of cover 254 is to block or diminish the light at the region which is closer to the preliminary gate 246, attracting the pupae closer to the gate 246 so as to facilitate streaming thereof toward the flow-control chamber 220 when the gate 246 is opened.

The cover can be attached to the preliminary gate 246, movable therewith when it transitions between the closed and open positions, or it can be attached to other immovable portions of the chamber 240, such as the sidewalls of the preliminary separation chamber 240.

The dimensions of the cover 254 can be selected to achieve a desired dark region adjacent gate 246. In some implementations, the rear portion of the cover 254 can be contoured or include a cut-out, as illustrated throughout FIGS. 5A-6, for easier placement of the bowl 244 in the chamber 240.

In use, both of the preliminary gate 246 and the flow control gate 226 can be set to the closed position at the beginning of the procedure, as shown in FIG. 5A. The preliminary separation chamber 240 can be filled with water (or other suitable fluid), and a bowl 244 with non-adult insects can be placed within the water, allowing non-adult insects smaller than the mesh size of the sieve 245 to flow into the surrounding water, and optionally swim toward the darker area near the preliminary gate 246 is a cover 254 is also provided.

Figure 5B:
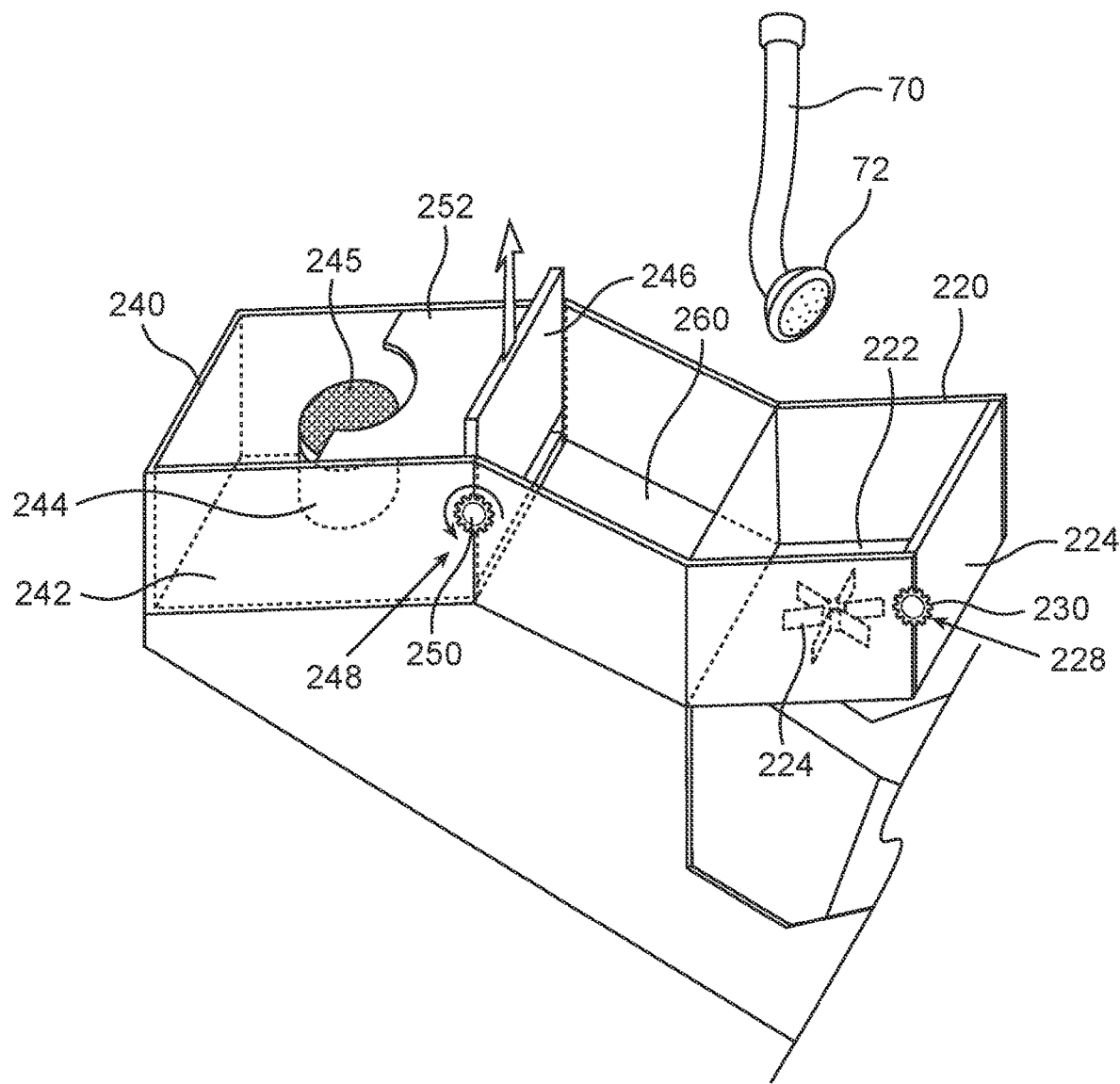
FIGS. 5B-5C show partial views of a portion of the separation apparatus of FIG. 5A in various stages of components or chambers thereof.
Figure 6:
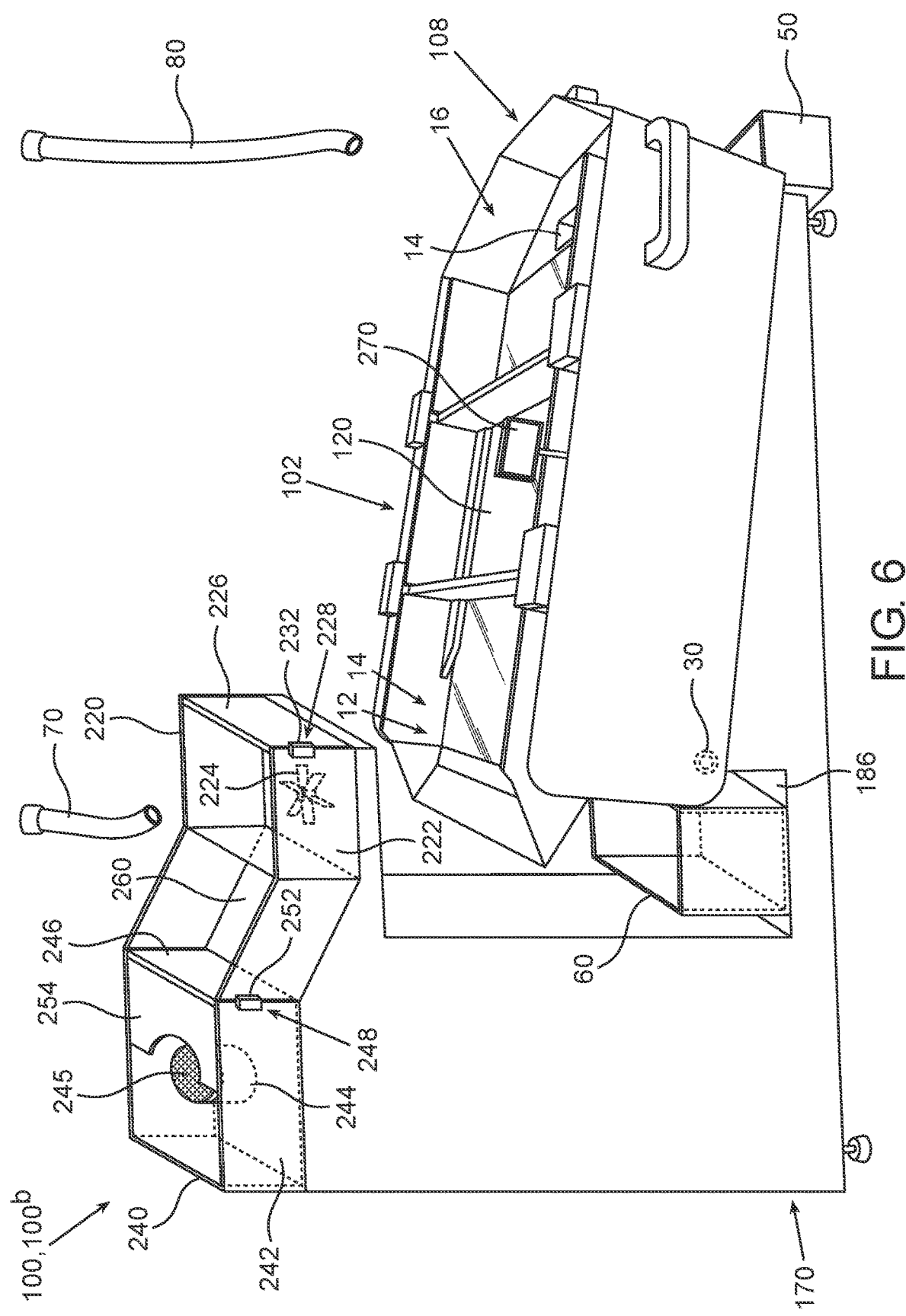
FIG. 6 shows yet another embodiment of a separation apparatus.

The preliminary gate 246 can then be opened, for example by utilizing preliminary gate displacement mechanism 248, allowing the mixture of water with non-adult insects to flow, optionally through guide channel 260, into the flow-control chamber 220, while the flow control gate 226 is still in the closed position, as shown in FIG. 5B. The mixture within flow-control can be optionally stirred with stirrer 224.

Figure 5C:
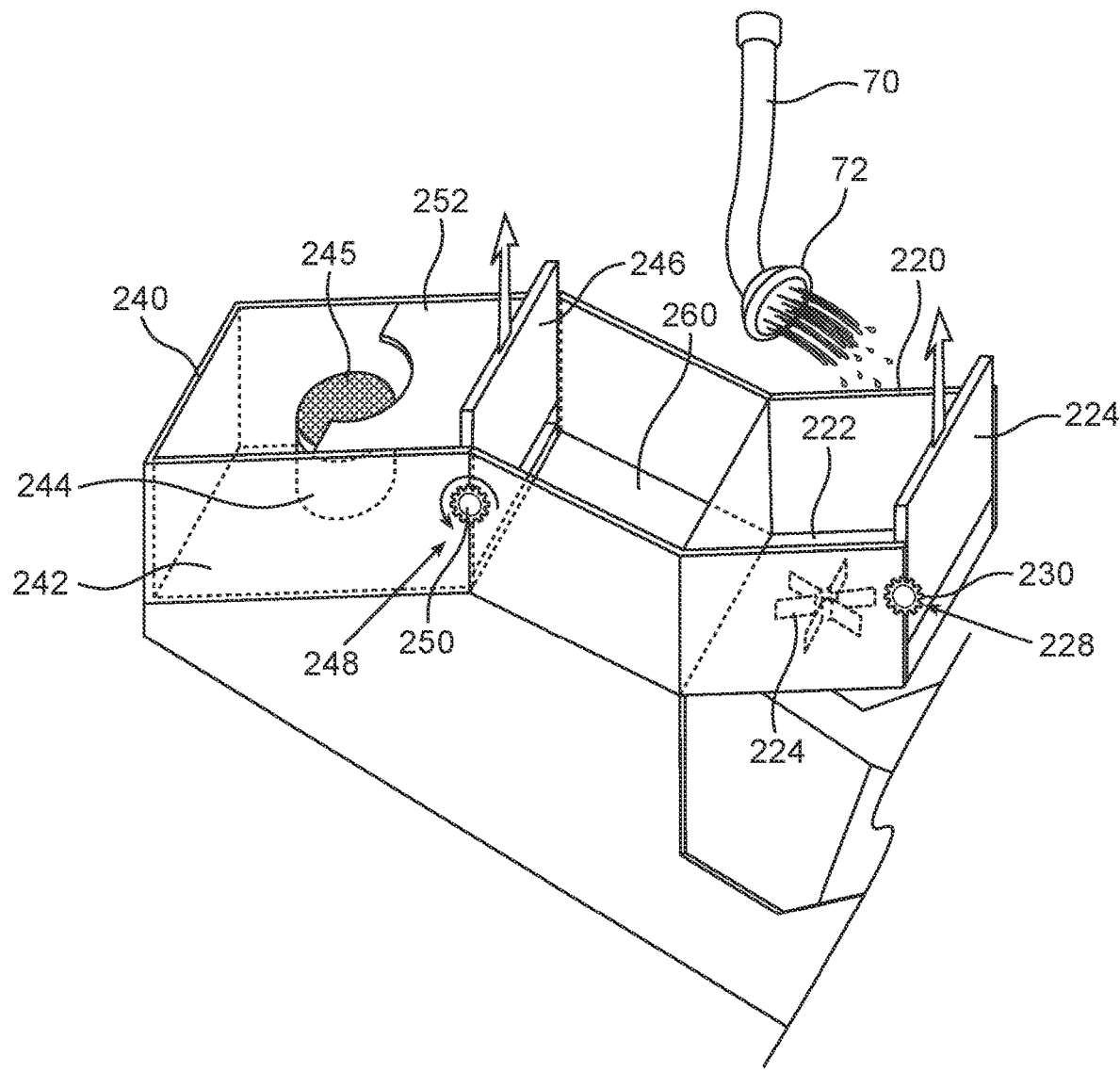

As shown in FIG. 5C, the flow control gate 226 can then be opened, for example by utilizing control gate displacement mechanism 228, allowing the mixture of water with non-adult insects to flow into the inclinable tub 102. Additional water may be poured or sprayed into the flow control chamber 220 through inflow pipe 70, to facilitate flow of all non-adult insects from the chamber 220 into tub 102.

In some embodiments, either one of the flow-control chamber 220, the preliminary separation chamber 240, or both, can be integrally formed with or otherwise affixed to the inclinable tub 102. FIG. 5A shows an embodiment 100*a* of the separation apparatus, in which both the flow-control chamber 220 and the preliminary separation chamber 240 are integrally formed with the inclinable tub 102. In such embodiments, the inclination of both chambers 220 and 240 may change along with the rest of the inclinable tub 102 as it pivots about pivot axis 30.

Is some embodiments, either one of the flow-control chamber 220, the preliminary separation chamber 240, or both, can be integrally formed with or otherwise affixed to the support base 170. FIG. 6 shows an embodiment 100*b* of the separation apparatus, in which both the flow-control chamber 220 and the preliminary separation chamber 240 are integrally formed with the support base 170. In such embodiments, the inclination of both chambers 220 and 240 is not affected by the orientation of inclinable tub 102.

In yet other embodiments, either one of the flow-control chamber 220, the preliminary separation chamber 240, or both, are provided as stand-alone components which are not integrally formed with and are not attached to the inclinable tub 102 or support base 170 (embodiments not shown), and are placed relative to the rear portion of the inclinable tub 102 to allow fluid communication there-between as described above. It is to be understood that in any embodiments, the position of the flow control gate 226 relative to the rear portion 104 of the tub 102 is selected to allow water mixture with non-adult insects to flow therefrom into the tub 102 without spilling. Similarly, the position of the preliminary gate 246 relative to the flow-control chamber 220, or relative to the guide channel 260 when provided, is selected to allow water mixture with non-adult insects to flow therefrom into the flow-control chamber 220, optionally along guide channel 260, without spilling.

In some embodiments, the separation apparatus 100 further comprises a washing pipe 80 in fluid communication with the front inflow space 16 of the inclinable tub 102, configured to pour rinse water through the inflow space 16 along the front portion 108 so as to wash away larger non-adult insects, such as female pupae, that remain in the tub 102, after transitioning the tub 102 to the front-upward inclination. The opening of washing pipe 70, from which rinse water exit the pipe 80, can be positioned above the front inflow space 16, oriented to direct the water flowing therefrom toward the adjustable bars 136 of the tub 102. The term "pipe" is non-limiting, and can include a rigid pipe, a flexible hose, a faucet and the like. In some embodiments, the washing pipe 80 further includes a washing sprayer 82 at its end portion, as illustrated for example, in FIG. 5A. In other embodiments, the washing pipe 80 is open ended without including a sprayer, as illustrated for example in FIG. 6.

In some embodiments, the separation apparatus 100 further comprises a front pan support 184 integrally formed with or otherwise affixed to the support base 170 at a front portion thereof, configured to support a front pan 50 that can be placed therein or thereon, below the front outflow space 14 of the tub 102. In some embodiments, the separation apparatus 100 further comprises a rear pan support 186 integrally formed with or otherwise affixed to the support base 170 at a rear portion thereof, configured to support a rear pan 60 that can be placed therein or thereon, below the rear portion 104 of the tub 102.

FIG. 5A illustrates an exemplary embodiment of a support base 170 provided with both a front pan support 184 and a rear pan support 186 integrally formed therewith and extending from the support base sidewalls 172 in the front and rear directions, respectively. While shown in the form of chambers defining an enclosed inner space within which pans 50 or 60 can be placed, it is to be understood that other structures for supporting such pans are contemplated, such as being formed as a plate on which a pan can be placed, without any sidewalls around the pan (see for example in FIG. 6 for rear pan support 186).

In some embodiments, one or two of the pans can be placed on the ground or any other structure that is not integrally formed with or attached to support base 170, such as shown for the exemplary embodiment of FIG. 6, in which the rear pan 60 can be placed on a rear pan support 186, while the front pan 50 is simply placed on the ground below the front outflow space 14 and in front of the support base 170.

As mentioned above, any movable component, as well as any sensing component, of the separator apparatus, can be either mechanically/manually operated, or electrically operated and controlled. FIG. 6 shows one example of a separation apparatus 100 that can include an interface, such as a display or touch screen 270 that can display reading from gauge indicators 164 that can include sensors as described above (not shown), and can control the operation of any of the bar positioning assemblies 148, the extensible members 178, the actuators 232 of control gate displacement mechanism 228, the actuators 252 of preliminary gate displacement mechanism 248, the stirrer 224, and flow through inflow pipe 70 or washing pipe 80.

Figure 7:
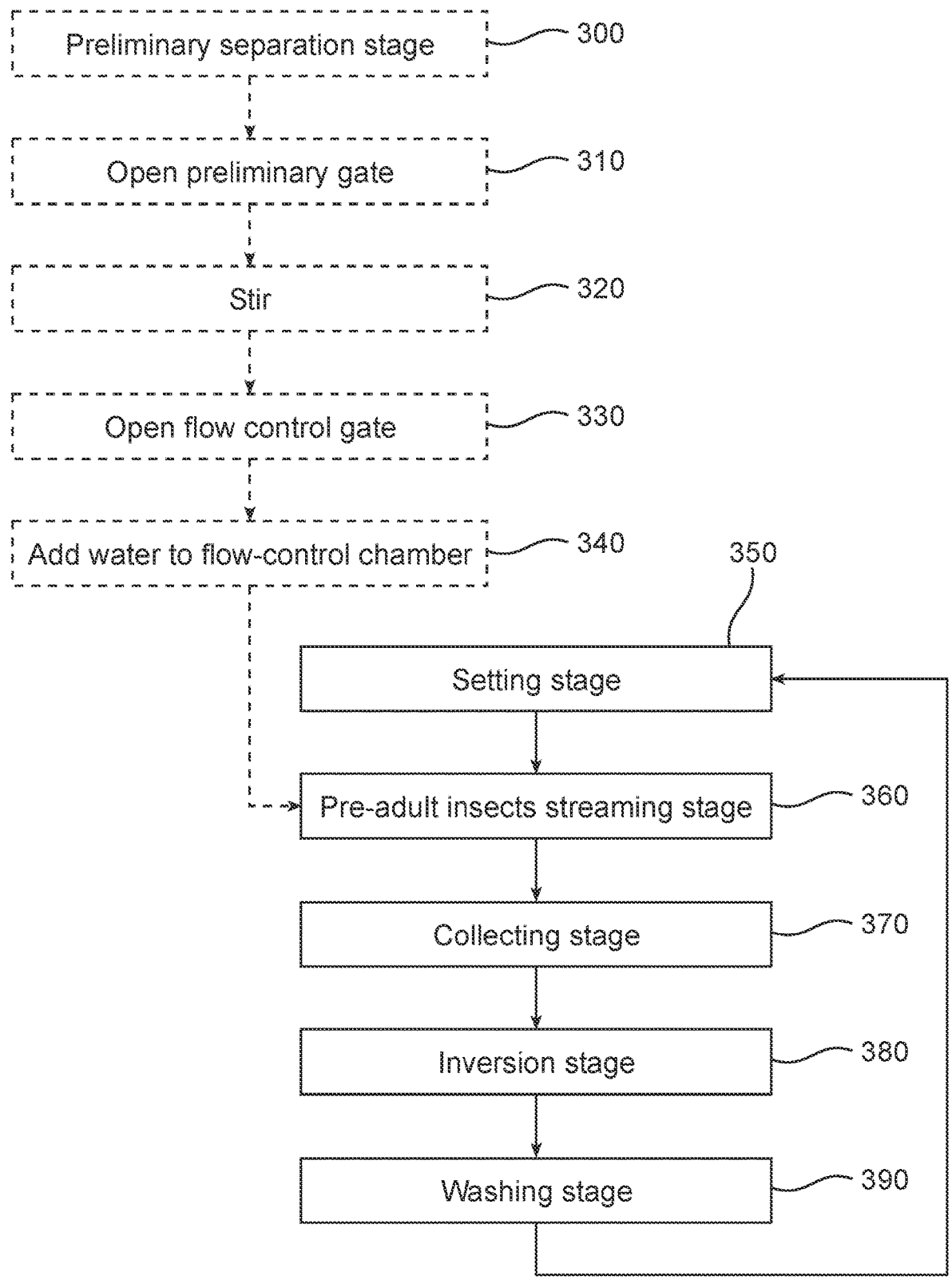
FIG. 7 illustrates a high-level flow chart of a method for separating non-adult insects, according to some embodiments.

FIG. 7 illustrates a high-level flow chart of a method for separating non-adult insects, according to some embodiments. In the setting stage 350, a separation apparatus 100 is provided with an inclinable tub 102, which is pivotably attached to a support base 170, wherein the inclinable tub 102 is in a front-downward inclination. If the separation apparatus 100 has its inclinable tub 102 in another orientation, such as a front-upward inclination, stage 350 include rotating the inclinable tub 102 about pivot axis 30 to the front-downward inclination. Otherwise, stage 350 can simply include verification that the inclinable tub 102 is indeed oriented at the front-downward inclination, preferably at a desired positive angle of inclination a. If the inclinable tub 102 is oriented at any other angle, step 350 can include rotating the inclinable tub 102 about pivot axis 30 to the desired positive angle of inclination a.

In the pre-adult insects streaming stage 360, which a mixture of fluid and non-adult insects, such as water with pupae, is supplied to rear portion 104 of the inclinable tub 102, through rear flow space 12. Supplying this mixture can be achieved either by manually pouring it from a pan or any other container, or by streaming it from a flow-control chamber 220.

In stage 370, the mixture is allowed to flow over the flow surface 120, through at least one gap 190 defined between a lower edge 139 of a corresponding adjustable bar 136 and the flow surface 120, and out of the inclinable tub, optionally into a front pan placed below a front outflow space 14 of the tub 102. This stage can include verifying that there is no more flow along the flow surface 120 prior to proceeding to stage 380.

In the inversion stage 380, the inclinable tub 102 is rotated about pivot axis 30 to a front-upward inclination, optionally to a desired negative angle of inclination (3. In this stage, at least one extensible member 178, and optionally two or more extensible members 178, are utilized to facilitate the rotational movement of the tube 102, as described above.

In the washing stage 390, rinse water are poured through the front inflow space 16 to the front portion 108 of the inclinable tub, allowing the water with any non-adult insects that remain in the tub 102, such as female pupae, to be washed and poured into a rear pan 60, for example.

In some embodiments, rotational movement of the inclinable tub 102 is performed manually, for example, by grasping handle of the tub 102 such as front handle 113 or any side handle 114, wherein the extensible members 178 passively assist in such rotational movement of the tub 102, relieving the effort required from the user of the apparatus. In other embodiments, rotational movement of the inclinable tub 102 is facilitated by at least one electrically operated and controlled extensible member 178.

In some embodiments, orienting the inclinable tub 102 to the front-downward inclination is performed by rotating the inclinable tub 102 in a downward direction until a downward rotational stopping feature of the apparatus prevents further rotational movement in the same direction, wherein the downward rotational stopping feature can be implemented as offset extension 176 or any other form described above.

As mentioned above, the mixture of fluid and non-adult insects can be streamed to the rear portion 104 of inclinable tub 102 from a flow-control chamber 220. Thus, in some embodiments, an optional stage 330 performed prior to stage 360, or simultaneously with stage 360 to achieve stage 360, can include opening a flow control gate 226 of a flow-control chamber 220 that contained such a mixture therein in a closed position of the flow control gate 226. A control gate displacement mechanism 228 can be employed in this stage, as described above, to transition the gate 226 from a closed position to an open position, defining a desirable space through which the mixture can flow to achieve a desired flow rate into the tub 102.

An optional stage 340 can include adding water, supplied for example through inflow pipe 70, into the flow-control chamber 220. This stage can be performed after stage 330, and can terminate at any time before the stage of inverting 380.

An optional stage 320 can include stirring the mixture within the flow-channel chamber 220, for example by employing stirrer 224. This stage is preferably performed in a closed position of the flow control gate 226, prior to opening it in stage 330.

In some embodiments, the mixture of fluid with pre-adult insects can be supplied into the flow-control chamber 220 from a preliminary separation chamber 240. In such cases, the method can include additional optional stages 300 and 310 performed prior to stage 330. An optional preliminary separation stage 300, a sieved bowl 244 containing unsorted pre-adult insects, such as larvae and pupae, is immersed in a volume of liquid (e.g., water) contained in a preliminary separation chamber 240 provided with a preliminary gate 246 kept in a closed position in this stage. This stage can include waiting for a minimal period of time during which non-adult insects, such as pupae, can pass through the sieve of the bowl into the surrounding water, and optionally swim toward the preliminary gate 246 if the flow-control chamber 220 also includes a cover 254 as described above.

In stage 310, the preliminary gate 246 is opened, allowing the mixture of fluid with pre-adult insects to flow from the preliminary separation chamber 240, optionally through a guide channel 260, into flow-control chamber 220.

If another batch of pre-adult insects is to be sorted, steps 350 to 390 can be repeated any numerous numbers of time, wherein the setting stage 350 after each washing stage 390 includes reorienting the inclinable tub 102 back to the front-downward inclination, preferably to the desired positive angle of inclination a.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A separation apparatus, comprising:
a support base;
an inclinable tub pivotably coupled to the support base about a pivot axis, the inclinable tube comprising:
  a rear portion defining a rear flow space;
  a front portion defining a front outflow space;
  two tub sidewalls extending between the rear portion and the front portion;
  a tub floor defining a flow surface;
  at least one adjustable bar extending between the tub sidewalls, and defining a gap having a gap height between a lower edge of the adjustable bar and the flow surface;
  a bar positioning assembly configured to increase or decrease the gap height by adjusting the position of the adjustable bar relative to the flow surface;
at least one extensible member comprising a member upper end coupled to the inclinable tub, and a member lower end coupled to the support base;
wherein the inclinable tub is movable between a front-downward inclination of the flow surface, defining a positive inclination angle α between a horizontal plane and the flow surface, and a front-upward inclination of the flow surface, defining a negative inclination angle between a horizontal plane and the flow surface.

Example 2. The separation apparatus of any example herein, particularly example 1, wherein the at least one adjustable bar comprises a plurality of adjustable bars, and wherein the gap defined by the adjustable bar closest to the rear portion has a greater gap height than that of the gap defined by the adjustable bar closest to the front portion.

Example 3. The separation apparatus of any example herein, particularly any one of examples 1 or 2, wherein the bar positioning assembly comprises at least one adjustment bolt engaged with the adjustment bar, wherein rotation of the adjustment bolt is configured to facilitate movement of the adjustment bar in a direction perpendicular to the flow surface.

Example 4. The separation apparatus of any example herein, particularly any one of examples 1 to 3, wherein the bar positioning assembly further comprises at least one spring pressed between the adjustable bar and the tub floor, configured to bias the adjustable bar away from the tub floor in the absence of higher counter-forces applied to the adjustable bar.

Example 5. The separation apparatus of any example herein, particularly any one of examples 1 to 4, wherein the adjustable bar is coupled to at least one sidewall by at least one mount that is affixed to the corresponding sidewall, and wherein a lateral end portion of the adjustable bar is movably coupled to the mount.

Example 6. The separation apparatus of any example herein, particularly example 5, wherein each tub sidewall comprises an outer sidewall and an inner sidewall, wherein the mount is disposed between the outer sidewall and the inner sidewall, and wherein the gap extends between the inner sidewalls.

Example 7. The separation apparatus of any example herein, example 6, wherein at least one inner wall comprises a guide slot, and wherein the adjustable bar comprises at least one main recess placed over the guide slot.

Example 8. The separation apparatus of any example herein, particularly any one of examples 1 to 7, further comprising at least one step positioned at the corner of convergence between the tub sidewall and the adjustable bar, wherein the adjustable bar comprises a complementary step recess, and wherein the height of the step recess is shorter than the height of the step.

Example 9. The separation apparatus of any example herein, particularly any one of examples 1 to 8, wherein the bar positioning assembly further comprises at least one gauge indicator which is configured to provide an indication of the height of gap.

Example 10. The separation apparatus of any example herein, particularly example 9, wherein the gauge indicator is a dial indicator comprising a display portion, a stem extending from the display portion, and a plunger extending from the stem and terminating with a contact point pressed against an upper edge of the adjustable bar.

Example 11. The separation apparatus of any example herein, particularly any one of examples 1 to 10, further comprising a front floor opening extending through the tub floor in the region of the front portion, wherein the front floor opening defines the front outflow space.

Example 12. The separation apparatus of any example herein, particularly any one of examples 1 to 10, wherein the positive inclination angle α is in the range between 5 and 30 degrees.

Example 13. The separation apparatus of any example herein, particularly example 12, wherein the positive inclination angle α is in the range between 5 and 15 degrees.

Example 14. The separation apparatus of any example herein, particularly any one of examples 1 to 13, wherein the absolute value of the negative inclination angle β is at least two times greater than that of the positive inclination angle α.

Example 15. The separation apparatus of any example herein, particularly example 14, wherein the absolute value of the negative inclination angle β is at least three times greater than that of the positive inclination angle α.

Example 16. The separation apparatus of any example herein, particularly any one of examples 1 to 15, wherein the negative inclination angle β is in the range between 25 and 35 degrees.

Example 17. The separation apparatus of any example herein, particularly any one of examples 1 to 16, wherein the extensible member is a gas spring.

Example 18. The separation apparatus of any example herein, particularly any one of examples 1 to 17, wherein the maximal stroke of the extensible member is configured to match the maximal the negative inclination angle β.

Example 19. The separation apparatus of any example herein, particularly any one of examples 1 to 17, further comprising a downward rotational stopping feature configured to prevent further rotation of the inclinable tub about the pivot axis beyond a maximal predefined positive inclination angle α.

Example 20. The separation apparatus of any example herein, particularly example 19, further comprising at least one offset extension extending downward from the inclinable tub, wherein the member upper end of a corresponding extensible member is attached to the offset extension, and wherein the offset extension defines the downward rotational stopping feature.

Example 21. The separation apparatus of any example herein, particularly example 19, wherein at least one of the front wall and/or the tub sidewalls, has a lower edge defining the downward rotational stopping feature.

Example 22. The separation apparatus of any example herein, particularly any one of examples 1 to 21, further comprising a flow-control chamber which is in fluid communication with the rear portion of the inclinable tub, wherein the flow-control chamber comprises a flow control gate movable between a closed position and an open position.

Example 23. The separation apparatus of any example herein, particularly example 22, further comprising an inflow pipe in fluid communication with the flow-control chamber.

Example 24. The separation apparatus of any example herein, particularly any one of examples 22 or 23, wherein the flow-control chamber further comprises a stirrer.

Example 25. The separation apparatus of any example herein, particularly any one of examples 22 to 24, further comprising a preliminary separation chamber in fluid communication with the flow-control chamber, wherein the preliminary separation chamber comprises a preliminary gate movable between a closed position and an open position.

Example 26. The separation apparatus of any example herein, particularly example 25, wherein the preliminary separation chamber is spaced away from the flow-control chamber, and wherein the separation apparatus further comprises a guide channel extending between the preliminary separation chamber and the flow-control chamber.

Example 27. The separation apparatus of any example herein, particularly any one of examples 25 or 26, wherein the preliminary separation chamber further comprises a cover extending rearward from the preliminary gate.

Example 28. The separation apparatus of any example herein, particularly any one of examples 1 to 27, further comprising a washing pipe in fluid communication with a front inflow space of the inclinable tub.

Example 29. The separation apparatus of any example herein, particularly any one of examples 1 to 28, wherein the bar positioning assembly comprises a respective electrically operable mechanism arranged to: receive a respective user input; and adjusting the position of the adjustable bar relative to the flow surface responsive to the received respective user input.

Example 30. The separation apparatus of any example herein, particularly any one of examples 1 to 29, wherein the at least one extensible member comprises a respective electrically operable mechanism arranged to: receive a respective user input; and, responsive to the received respective user input, extend or retract the at least one extensible member to move the inclinable tub to a respective positive inclination angle α or negative inclination angle β.

Example 31. A method for separating non-adult insects, comprising:
  supplying a mixture of fluid and non-adult insects to a rear portion of an inclinable tub while the inclinable tub is in a front-downward inclination of a flow surface thereof, such that the fluid with non-adult insects is urged to flow over the flow surface from a rear portion of the inclinable tub, through at least one gap formed by at least one adjustable bar of the inclinable tub, toward a front portion of the inclinable tub;
  collecting the fluid with non-adult insects that passed through the at least one gap and out of the inclinable tub, through a front outflow space of the inclinable tub;
  utilizing at least one extensible member for rotating the inclinable tub about a pivot axis to a front upward inclination of the flow surface; and
  pouring rinse water through a front inflow space of the inclinable tub.

Example 32. The method of any example herein, particularly example 31, further comprising a step of setting the inclinable tub back to the front downward inclination of the flow surface, and repeatedly performing the steps of the method for a desired number of iterations.

Example 33. The method of any example herein, particularly any one of examples 31 or 32, wherein supplying a mixture of fluid and non-adult insects to a rear portion of an inclinable tub comprises streaming the mixture of fluid and non-adult insects from a flow-control chamber into the rear portion of the inclinable tub, by opening a flow control gate of the flow-control chamber.

Example 34. The method of any example herein, particularly example 33, further comprising adding water into the flow-control chamber through an inflow pipe.

Example 35. The method of any example herein, particularly any one of examples 33 or 34, further comprises stirring the mixture of fluid and non-adult insects by a stirrer disposed within the flow-control chamber.

Example 36. The method of any example herein, particularly any one of examples 33 to 35, further comprising streaming the mixture of fluid and non-adult insects from a preliminary chamber into the flow-control chamber, by opening a preliminary gate of the preliminary chamber prior to opening the flow control gate.

Example 37. The method of any example herein, particularly example 36, further comprising immersing a sieved bowl with unsorted pre-adult insects in a volume of liquid contained in the preliminary chamber, while the preliminary gate is in a closed state.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

In view of the many possible embodiments to which the principles of the disclosure may be applied, it should be recognized that the illustrated embodiments are only preferred examples and should not be taken as limiting the scope. Rather, the scope is defined by the following claims. We therefore claim all that comes within the scope and spirit of these claims.

The invention claimed is:

1. A separation apparatus for separation of non-adult insects, comprising:
    a support base;
    an inclinable tub pivotably coupled to the support base about a pivot axis, the inclinable tub comprising:
        a rear portion defining a rear flow space;
        a front portion defining a front outflow space;
        two tub sidewalls extending between the rear portion and the front portion;
        a tub floor defining a flow surface;
        a plurality of height-adjustable bars, each extending between the tub sidewalls and defining a gap having a gap height between a lower edge of the corresponding height-adjustable bar and the flow surface in a direction perpendicular to the flow surface;
        a plurality of bar positioning assemblies, each configured to increase or decrease the gap height of a corresponding one of the plurality of height-adjustable bars by independently adjusting the position of the corresponding height-adjustable bar relative to the flow surface, without affecting the gap height of any other one of the plurality of height-adjustable bars;
    at least one extensible member comprising a member upper end coupled to the inclinable tub, and a member lower end coupled to the support base;
wherein the at least one extensible member is configured to transition the inclinable tub between a front-downward inclination of the flow surface, defining a positive inclination angle $\alpha$ between a horizontal plane and the flow surface, and a front-upward inclination of the flow surface, defining a negative inclination angle $\beta$ between a horizontal plane and the flow surface.

2. The separation apparatus of claim 1, wherein the gap defined by the height-adjustable bar closest to the rear portion has a greater gap height than that of the gap defined by the height-adjustable bar closest to the front portion.

3. The separation apparatus of claim 1, wherein at least one of the plurality of bar positioning assemblies comprises at least one adjustment bolt engaged with the corresponding height-adjustable bar, wherein rotation of the adjustment bolt is configured to facilitate movement of the corresponding height-adjustable in a direction perpendicular to the flow surface.

4. The separation apparatus of claim 1, wherein at least one of the plurality of bar positioning assemblies further comprises at least one spring pressed between the corresponding height-adjustable bar and the tub floor, configured to bias the height-adjustable bar away from the tub floor in the absence of higher counter-forces applied to the corresponding height-adjustable bar.

5. The separation apparatus of claim 1, wherein at least one of the plurality of height-adjustable bars is coupled to at least one sidewall by at least one mount that is affixed to the corresponding sidewall, and wherein a lateral end portion of the corresponding height-adjustable bar is movably coupled to the mount.

6. The separation apparatus of claim 5, wherein each tub sidewall comprises an outer sidewall and an inner sidewall, wherein the mount is disposed between the outer sidewall and the inner sidewall, and wherein the gap extends between the inner sidewalls.

7. The separation apparatus of claim 6, wherein at least one inner wall comprises a guide slot, and wherein the corresponding at least one height-adjustable bar comprises at least one main recess placed over the guide slot.

8. The separation apparatus of claim 1, further comprising at least one step positioned at a corner of convergence between the tub sidewall and at least one of the plurality of height-adjustable bars, wherein the corresponding height-adjustable bar comprises a complementary step recess, and wherein the height of the step recess is shorter than the height of the step.

9. The separation apparatus of claim 1, wherein at least one of the plurality of bar positioning assemblies further comprises at least one gauge indicator which is configured to provide an indication of the height of gap.

10. The separation apparatus of claim 9, wherein the gauge indicator is a dial indicator comprising a display portion, a stem extending from the display portion, and a plunger extending from the stem and terminating with a contact point pressed against an upper edge of the corresponding height-adjustable bar.

11. The separation apparatus of claim 1, further comprising a front floor opening extending through the tub floor in the region of the front portion, wherein the front floor opening defines the front outflow space.

12. The separation apparatus of claim 1, wherein the positive inclination angle $\alpha$ is in the range between 5 and 30 degrees.

13. The separation apparatus of claim 1, wherein the absolute value of the negative inclination angle $\beta$ is at least two times greater than that of the positive inclination angle $\alpha$.

14. The separation apparatus of claim 1, wherein the negative inclination angle $\beta$ is in the range between 25 and 35 degrees.

15. The separation apparatus of claim 1, wherein the extensible member is a gas spring.

16. The separation apparatus of claim 1, wherein the maximal stroke of the extensible member is configured to match the maximal negative inclination angle $\beta$.

17. The separation apparatus of claim 1, further comprising a downward rotational stopping feature configured to prevent further rotation of the inclinable tub about the pivot axis beyond a maximal predefined positive inclination angle $\alpha$.

18. The separation apparatus of claim 17, further comprising at least one offset extension extending downward from the inclinable tub, wherein the member upper end of a corresponding extensible member is attached to the offset extension, and wherein the offset extension defines the downward rotational stopping feature.

19. The separation apparatus of claim 17, wherein at least one of the front wall and/or the tub sidewalls, has a lower edge defining the downward rotational stopping feature.

20. The separation apparatus of claim 1, further comprising a flow-control chamber which is in fluid communication with the rear portion of the inclinable tub, wherein the flow-control chamber comprises a flow control gate movable between a closed position and an open position.

21. The separation apparatus of claim 20, further comprising an inflow pipe in fluid communication with the flow-control chamber.

22. The separation apparatus of claim 20, wherein the flow-control chamber further comprises a stirrer.

23. The separation apparatus of claim 20, further comprising a preliminary separation chamber in fluid communication with the flow-control chamber, wherein the preliminary separation chamber comprises a preliminary gate movable between a closed position and an open position.

24. The separation apparatus of claim 23, wherein the preliminary separation chamber is spaced away from the flow-control chamber, and wherein the separation apparatus further comprises a guide channel extending between the preliminary separation chamber and the flow-control chamber.

25. The separation apparatus of claim 23, wherein the preliminary separation chamber further comprises a cover extending rearward from the preliminary gate.

26. The separation apparatus of claim 1, further comprising a washing pipe in fluid communication with a front inflow space of the inclinable tub.

27. The separation apparatus of claim 1, wherein at least one of the plurality of bar positioning assemblies comprises a respective electrically operable mechanism arranged to adjust the position of the corresponding height-adjustable bar relative to the flow surface.

28. The separation apparatus of claim 1, wherein the at least one extensible member comprises a respective electrically operable mechanism arranged to extend or retract the at least one extensible member to move the inclinable tub to a respective positive inclination angle $\alpha$ or negative inclination angle $\beta$.

29. A method for separating non-adult insects, comprising:
supplying a mixture of fluid and non-adult insects to a rear portion of an inclinable tub while the inclinable tub is in a front-downward inclination of a flow surface thereof, such that the fluid with non-adult insects is urged to flow over the flow surface from a rear portion of the inclinable tub, through at least one gap formed by at least one adjustable bar of the inclinable tub, toward a front portion of the inclinable tub;
collecting the fluid with non-adult insects that passed through the at least one gap and out of the inclinable tub, through a front outflow space of the inclinable tub;
utilizing at least one extensible member for rotating the inclinable tub about a pivot axis to a front upward inclination of the flow surface; and
pouring rinse water through a front inflow space of the inclinable tub.

30. The method of claim 29, wherein supplying a mixture of fluid and non-adult insects to a rear portion of an inclinable tub comprises streaming the mixture of fluid and non-adult insects from a flow-control chamber into the rear portion of the inclinable tub, by opening a flow control gate of the flow-control chamber.

* * * * *